US009850282B2

(12) United States Patent
Rucman

(10) Patent No.: US 9,850,282 B2
(45) Date of Patent: Dec. 26, 2017

(54) STABLE PENTADECAPEPTIDE SALTS, A PROCESS FOR PREPARATION THEREOF, A USE THEREOF IN THE MANUFACTURE OF PHARMACEUTICAL PREPARATIONS AND A USE THEREOF IN THERAPY

(71) Applicant: DIAGEN D.O.O., Ljubljana Smartno (SI)

(72) Inventor: Rudolf Rucman, Ljubljana Smartno (SI)

(73) Assignee: DIAGEN D.O.O., Ljubljana Šmartno (SI)

( * ) Notice: Subject to any disclaimer, the term of this patent is extended or adjusted under 35 U.S.C. 154(b) by 0 days.

(21) Appl. No.: 14/774,457

(22) PCT Filed: May 9, 2013

(86) PCT No.: PCT/SI2013/000026
§ 371 (c)(1),
(2) Date: Sep. 10, 2015

(87) PCT Pub. No.: WO2014/142764
PCT Pub. Date: Sep. 18, 2014

(65) Prior Publication Data
US 2016/0068572 A1   Mar. 10, 2016

(30) Foreign Application Priority Data

Mar. 13, 2013   (SI) .................................. 201300055

(51) Int. Cl.
| A61K 38/10 | (2006.01) |
| A61K 45/06 | (2006.01) |
| C07K 7/08 | (2006.01) |
| A23L 1/30 | (2006.01) |
| A23L 33/10 | (2016.01) |

(52) U.S. Cl.
CPC ................ C07K 7/08 (2013.01); A23L 33/10 (2016.08); A61K 38/10 (2013.01); A61K 45/06 (2013.01); A23V 2002/00 (2013.01)

(58) Field of Classification Search
CPC .... A61K 38/10; A61K 2300/00; A61K 45/06; A23L 1/30; A23V 2002/00; C07K 7/08
USPC ......... 514/15.6, 15.7, 16.5, 17.5, 17.7, 17.9, 514/18.2, 19.3, 1.7, 21.5, 3.7, 4.2; 530/326
See application file for complete search history.

(56) References Cited

U.S. PATENT DOCUMENTS 4,485,033 A * 11/1984 Kitao ...................... A61K 9/02
  252/1
5,238,921 A * 8/1993 Maruyama ........... C07K 5/0808
  514/15.7
6,288,028 B1 * 9/2001 Sikiric .................. C07K 14/47
  514/23
2011/0044914 A1 * 2/2011 Kohli ................... A61K 8/0216
  424/44

FOREIGN PATENT DOCUMENTS

| CN | 1296079 A | 5/2001 |
| WO | 2010/033240 A2 | 3/2010 |

OTHER PUBLICATIONS

Disorders from Merck Manual, pp. 1-7. Accessed on Sep. 12, 2016.*
Diseases from Merck Manual, pp. 1-7. Accessed on Sep. 12, 2016.*
Introduction to Cancer from Merck Manual, p. 1. Accessed Mar. 5, 2008.*
Clinical Aspects of Cancer from Merck Manual, pp. 1-4. Accessed Mar. 5, 2008.*
Dementia from Merck Manual, pp. 1-17. Accessed Jul. 29, 2009.*
Mattson MP, "Pathways towards and away from Alzheimer's disease," Nature, 2004, 430: 631-639.*
Auerbach et al, "Angiogenesis assays: Problems and pitfalls," Cancer and Metastasis Reviews, 2000, 19: 167-172.*
Gura T, "Systems for Idenfifying New Drugs Are Often Faulty," Science, 1997, 278: 1041-1042.*
Hepatitis A from Mayo Clinic, pp. 1-2. Accessed Aug. 9, 2012.*
Jain RK, "Barriers to Drug Delivery in Solid Tumors," Scientific American, 1994, 58-65.*
Sriram et al, "Experimental Allergic Encephalomyelitis: A Misleading Model of Multiple Sclerosis," Ann. Neurol., 2005, 58: 939-945.*
Steinman et al, "How to Successfully Apply Animal Studies in Experimental Allergic Encephalomyelitis to Research on Multiple Sclerosis," Ann. Neurol., 2006, 60: 12-21.*
International Search Report and Written Opinion of the International Searching Authority, PCT/SI2013/000026; dated Oct. 16, 2013.

(Continued)

Primary Examiner — Julie Ha
(74) Attorney, Agent, or Firm — Studebaker & Brackett PC

(57) ABSTRACT

Stable pentadecapeptide salts of formula (I):

(I)
```
                                          SEQ ID NO 1
Gly Glu Pro Pro Pro Gly Lys Pro Ala Asp Asp Ala
1               5                        10

Gly Leu Val · n BAA
    15
``` wherein n means 1, 2 or 3, and BAA means basic amino acid, a process for the preparation thereof, a process for the use thereof for the manufacture of pharmaceutical formulations in liquid and solid form and a use thereof for prevention, protection in treatment of diseases and disease conditions and for the preparation of formulations for use as food supplements are described.

33 Claims, 5 Drawing Sheets

(56) References Cited

OTHER PUBLICATIONS

Torkildsen Ø, Brunborg LA, Myhr KM, Bø L. The cuprizone model for demyelination. Acta Neurologica Scandinavica. May 1, 2008; 117(s188):72-6.

Sikirić P, Seiwerth S, Brcic L, Sever M, Klicek R, Radic B, Drmic D, Ilic S, Kolenc D. Revised Robert's cytoprotection and adaptive cytoprotection and stable gastric pentadecapeptide BPC 157. Possible significance and implications for novel mediator. Curr Pharm Des. Apr. 1, 2010; 16(10):1224-34.

Szabo S, Tache Y, Somogyi A. The legacy of Hans Selye and the origins of stress research: a retrospective 75 years after his landmark brief letter to the editor of nature. Stress 2012; 15:472-8.

Sikirić P, Petek M, Rucman R, et al. A new gastric juice peptide, BPC. An overview of the stomach-stress-organoprotection hypothesis and beneficial effects of BPC. J Physiol Paris 1993; 87:313-27.

Selye H. A syndrome produced by diverse nocuous agents. Nature 1936; 138:32.

Sikirić P, Seiwerth S, Rucman R, et al. Toxicity by NSAIDs. Counteraction by stable gastric pentadecapeptide BPC 157. Curr Pharm Des 2013; 19:76-83.

Sikirić P, Seiwerth S, Rucman R, et al. Focus on ulcerative colitis: stable gastric pentadecapeptide BPC 157. Curr Med Chem 2012; 9:126-32.

Sikirić P, Seiwerth S, Rucman R, et al. Stable gastric pentadecapeptide BPC 157: novel therapy in gastrointestinal tract. Curr Pharm Des 2011; 17:1612-32.

Bodanszky M. Peptide chemistry: a practical textbook. Springer-Verlag, 1988, p. 107.

Lloyd-Williams P, Albericio F, Giralt E. Chemical approaches to the synthesis of peptides and proteins. CRC Press, 1997, pp. 61-62.

Masson G, Selye H. Reaction generale d'adaptation. Ses indications pratiques. (General reaction of adaptation. Practical guidance.) Canadian Journal of Comparative Medicine. Nov. 1938; II(11):282-285. Google Translate.

Sikirić P, Seiwerth S, Brcic L, Blagaic AB, Zoricic I, Sever M, Klicek R, Radic B, Keller N, Sipos K, Jakir A, Udovicic M, Tonkic A, Kokic N, Turkovic B, Mise S, Anic T. Stable gastric pentadecapeptide BPC 157 in trials for inflammatory bowel disease (PL-10, PLD-116, PL 14736, Pliva, Croatia). Full and distended stomach, and vascular response. Inflammopharmacology 2006; 14:214-221.

\* cited by examiner

Fig. 3.

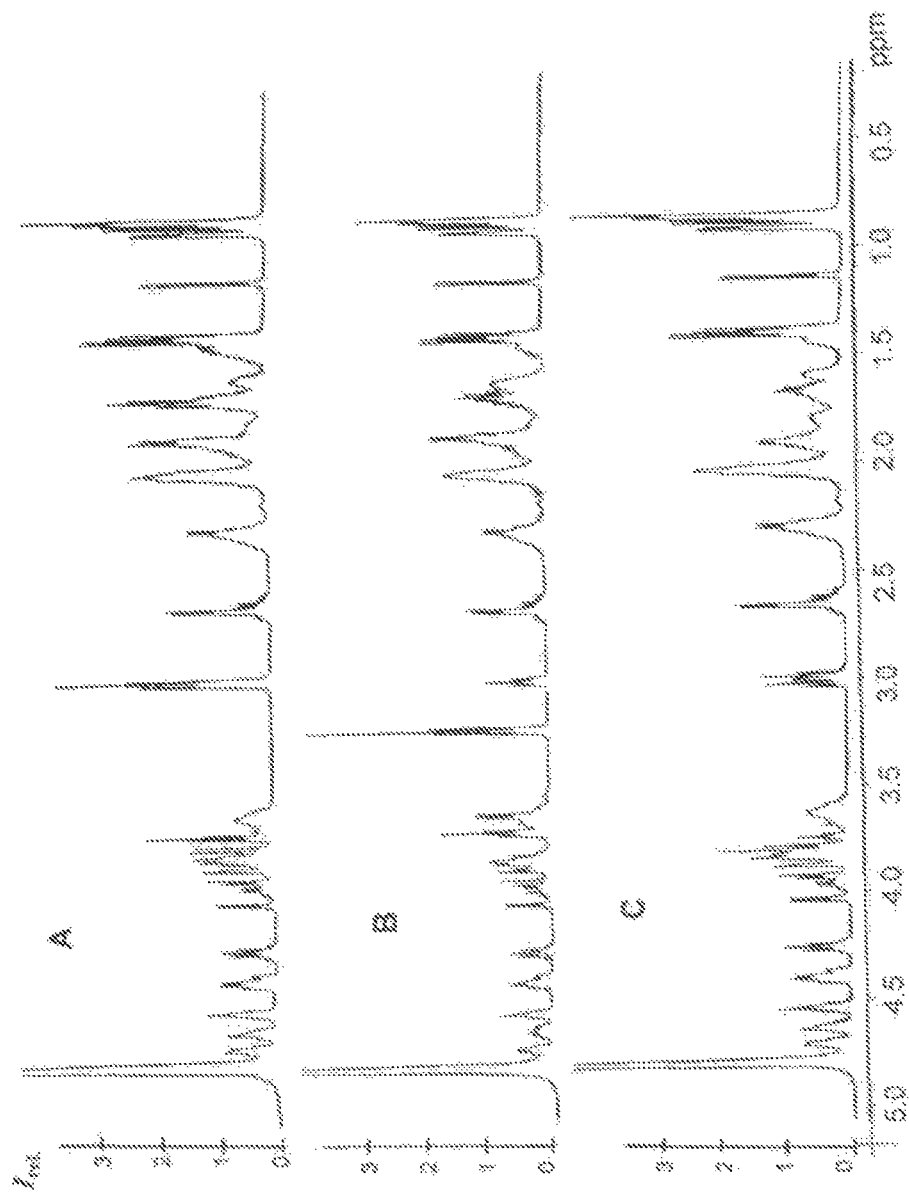

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Salts of SEQ ID NO 1 with basic amino acids

<400> SEQUENCE: 1

Gly Glu Pro Pro Pro Gly Lys Pro Ala Asp Asp Ala Gly Leu Val
1               5                   10                  15
```

STABLE PENTADECAPEPTIDE SALTS, A PROCESS FOR PREPARATION THEREOF, A USE THEREOF IN THE MANUFACTURE OF PHARMACEUTICAL PREPARATIONS AND A USE THEREOF IN THERAPY

TECHNICAL FIELD

The present invention belongs to the field of pharmaceutical chemistry and relates to new stable pentadecapeptide salts, hereinafter referred to also as bepecin salts of formula (I):

```
(I)
                                        SEQ ID NO: 1
Gly Glu Pro Pro Pro Gly Lys Pro Ala Asp Asp Ala
1               5                   10

Gly Leu Val · n BAA
        15
``` wherein n is 1, 2 or 3, and BAA is a basic amino acid, a process for the preparation thereof, a use thereof in the manufacture of pharmaceutical preparations and a use thereof in therapy.

Technical Problem

Numerous pharmacological studies have demonstrated a protective, regenerative and therapeutical activity of pentadecapeptide (abbr. BPC-157 or bepecin) having an amino acid sequence: Gly Glu Pro Pro Pro Gly Lys Pro Ala Asp Asp Ala Gly Leu Val (SEQ ID NO: 1) to both a human and animal organism. Until now, this peptide has always been used either in a free form or in an acetate form or as a salt with bases such as sodium salt. All these forms have been characterized by still not adequate stability in gastric juice, which particularly limits oral use of these compounds and simultaneously decreases their therapeutic value. It has therefore been necessary to manufacture this pentadecapeptide in a form which is substantially more stable both in gastric juice and at raised ambient temperature. Such form of the preparation could be used more successfully particularly in oral delivery into an organism. Due to higher stability an overall better effectiveness would be expected as well.

PRIOR ART

Pentadecapeptide BPC 157 or bepecin (abbr. for: Body Protecting Compound) has the following peptide sequence: Gly Glu Pro Pro Pro Gly Lys Pro Ala Asp Asp Ala Gly Leu Val (SEQ ID NO: 1) and represents the N-terminal part of a natural BPC protein which is actually present in the gastric juice of mammals. The natural BPC protein is obtained from human or animal gastric juice by means of complicated biochemical methods (U.S. Pat. No. 5,288,708). Irrespective of demanding work this way of obtaining is inappropriate also with regard to an uncertain source of raw material and a possible contamination with viruses. Therefore, by chemical synthesis (P. Sikirić, R. Ručman, B. Ručman, M. Petek, Peptides 1998, Proceed. of 25th EPS, Budapest 1998, p. 814; Z. Pflaum and R. Ručman, Acta Chim Slov., 2005, 52, 34-39) only the N-terminal part with the above stated sequence has been prepared. Surprisingly, it has been found that this fragment retained practically all effects of the natural BPC protein (EP 0572688 and U.S. Pat. No. 6,268,346). The N-terminal part with a sequence of 15 amino acids seems to be the most responsible for the biological activity of the entire protein. The compound is very interesting from a medical point of view, as it has effect to almost all organs at extremely low concentrations (in a range from ng to mg and more per a kilogram of body weight) and without any toxic or side effects.

Pharmacological studies have shown that pentadecapeptide bepecin (SEQ ID NO: 1) introduced in an organism has the following effects:

- on ulcers in any part of the gastrointestinal tract (P. Sikirić et al., Life Sci., 1994; 54, PL63-68); (P. Sikirić et al., Exp. Clin. Gastroenterol., 1991, 1, 17-20);
- antiinflamatory irrespective of etiology (P. Sikirić et al., J. Physiol. /Paris/, 1997, 91, 113-122);
- against an inflammatory disease of the gastrointestinal tract—Crohn's disease (Sikirić et al., J. Physiol. /Paris/, 2001, 95, 295-301);
- protective to liver and pancreas (Prkačin et al., J. Physiol. /Paris/, 2001, 95, 315-324);
- promotes healing of burns (D. Mikuš, P. Sikirić et al., Burns 2003, 29, 323-334; Burns, 2001, 127, 817-827);
- promotes healing of wounds (S. Seiwerth, P. Sikirić et al., J. Physiol. /Paris/, 1997, 91, 173-178);
- protective against radioactive radiation (P. Sikirić, M. Petek, R. Ručman, J. Physiol. /Paris/, 1993, 87, 313-327);
- promotes healing of bone fractures (B. Sebečić, V. Miklič, P. Sikirić et al., Bone, 1999, 24, 195-202);
- in interaction with adrenergic and dopaminergic systems it protects mucosas in stress conditions (P. Sikirić et al., Dig. Dis. Sci., 1997, 42, 661-671);
- antitumor effect in some types of tumors (ascites, melanoma) (P. Sikirić, M. Petek, R. Ručman, J. Physiol. /Paris/, 1993, 87, 313-327; S. Radeljak, S. Seiwert, P. Sikirić, Melanoma Research, 2004, 14 (4), A14-A15);
- antiviral effect on herpes viruses HSV-1 and HSV-2, LCM, CMV, influenza virus A and tick-borne encephalitis virus, P. Sikirić, R. Ručman, M. Petek, J. Physiol. /Paris/, 1993, 87, 313-327);
- promotes regeneration of ruptured nervous linkages (P. Sikirić et al., Dig. Dis. Sci., 41, 1604-1614; M. Gjurašin et al., Dig. Dis. Sci., 2003, 48, 1879);
- promotes healing of ruptured Achilles' tendon (M. Starešinić, P. Sikirić et al., J. Orthoped. Res., 2003, 21, 976-983);
- removes organic disorders associated with NO formation (P. Sikirić et al., Eur. J. Pharm., 1997, 332, 23-33).

Peptide bepecin as a constituent part of a living organism's own substance does not show any toxicity signs. Tests carried out on mice in order to determine $LD_{50}$ as well as with the purpose of obtaining data about acute, subchronic and chronic toxicity have been unsuccessful as this peptide applied intravenously, orally or intraperitoneally in a broad dose range from 10 ng to 100 mg/kg of body weight did not induce any toxic changes. In addition, the tests of teratogenicity and genotoxicity (*Salmonella* microsome test) proved no signs of such action.

The salts of synthethic pentadecapeptide BPC-157 are also disclosed in patents EP 0983300 and U.S. Pat. No. 6,288,028. These salts are slightly better than the original form, i.e. than free acid or acetate, yet they still lack sufficient stability in the gastric juice.

Solution to the Technical Problem

The fundamental problem to be solved is stability of the compound at an increased temperature, in particular the stability in gastric juice. The present invention relates to novel pentadecapeptide salts with basic amino acids having significantly improved thermal stability and also stability in gastric juice.

Gastric juice is a complex mixture of different compounds and the main components are: water, sodium chloride, hydrochloric acid, mucins, enzymes, particularly pepsin, and others. Gastric juice is mainly acidic; its pH value varies from 1 to 7 and exceptionally higher. Normal pH values are in the range from 2 to 5, which is also the range of the greatest activity of pepsin which decomposes polypeptides, peptides and proteins.

The present invention thus relates to novel stable pentadecapeptide salts of formula (I):

(I)
```
                                              SEQ ID NO: 1
Gly Glu Pro Pro Pro Gly Lys Pro Ala Asp Asp Ala
1               5                   10

Gly Leu Val · n BAA
        15
``` wherein n is 1, 2 or 3, and BAA is a basic amino acid.

As basic amino acids basic arginine, lysine, ornithine or others, in L-, D- or DL-form, preferably L-arginine, are used.

The present invention also relates to the process for the preparation of pentadecapeptide salts of formula (I), wherein pentadecapeptide of sequence (SEQ ID NO: 1) is reacted with basic amino acid BAA:

(I)
```
                                              SEQ ID NO: 1
Gly Glu Pro Pro Pro Gly Lys Pro Ala Asp Asp Ala
1               5                   10

Gly Leu Val + n BAA
        15

↓

SEQ ID NO: 1
Gly Glu Pro Pro Pro Gly Lys Pro Ala Asp Asp Ala
1               5                   10

Gly Leu Val · n BAA
        15
``` in a molar ratio from 1 to 3 moles of basic amino acid to 1 mole of pentadecapeptide with (SEQ ID NO: 1) in an aqueous solution at room temperature, the pH value of the formed solution is adjusted with titration, then the formed salt of formula (I) is isolated in the solid form by HPLC chromatography and lyophilisation.

In a preferred embodiment of the process of the invention the pH value of the solution obtained by a reaction of 1 mole of a basic amino acid with 1 mole of pentadecapeptide (SEQ ID NO: 1) is adjusted to 4.1 to 5.0, preferably to 4.60±0.05.

In another preferred embodiment of the process of the invention the pH value of the solution obtained by a reaction of 2 mol of a basic amino acid with 1 mol of pentadecapeptide (SEQ ID NO: 1) is adjusted to 6.7 to 7.8, preferably to 7.40±0.05.

The present invention further relates to a pharmaceutical formulation in a solid and liquid form containing a therapeutically effective amount of pentadecapeptide salt of the present invention for oral, intravenous, rectal, vaginal, intramuscular, local and other use. The present invention further relates to a pharmaceutical formulation containing in addition to pentadecapeptide salt of the present invention also one or more other active substances, preferably antibiotics or antioxidants.

The present invention further relates to a pharmaceutical formulation containing in addition to pentadecapeptide salt of the present invention also stability enhancing additives selected from the group comprising alkali metal and alkaline earth metal carbonates or hydrogen carbonates, preferably sodium hydrogen carbonate.

The present invention further relates to a pharmaceutical formulation containing in addition to pentadecapeptide salt of the present invention also stability enhancing additives selected from the group comprising sugars as trehalose, sorbitol or D-mannitol, but preferably D-mannitol.

The present invention further relates to a pharmaceutical formulation for use in prevention, prophylaxis and treatment of the following diseases and disease conditions:
- stress related diseases and disorders, ulcers in any part of the gastrointestinal tract, general antiinflammatory activity, gastrointestinal inflammatory disease, Crohn's disease, acute pancreatitis;
- organoprotective activity: protection of hepatic and pancreatic lesions, protection of endothelial cells, prevention of adhesion formation, prevention and treatment of myocardial infarction and brain stroke, protective effect in immune system;
- treatment of viral infections, particularly with hepatitis A virus, herpes strain influenza A virus and ARBO viruses, such as tick borne encephalitis, West Nile, dengue types 1-4, cytomegalovirus CMV and LCM virus, feline leukemia virus;
- treatment of melanoma and related tumors;
- accelerated healing of wounds, burns, bone fractures, regeneration of ruptured nerve linkages, Achilles' tendon and ruptured muscles, spinal cord injury;
- treatment of organic disorders associated with NO formation: hypertension, hypotension, anaphylaxis, circulatory and septic shock, aggregation of thrombocytes;
- treatment of neurological diseases and disorders: multiple sclerosis, myasthenia gravis, lupus erythematosus, neuropathy, dysfunction of somatosensory nerves, asthma, rhinitis, pemphigus and eczema;
- catecholaminergic dysfunction, schizophrenia, amphetamine, drug and alcohol withdrawal effects;
- prevention and elimination of disorders due to corticosteroids and NSAIDs;
- treatment of squamous degeneration of macula of the eye;
- as original therapy in all conditions, in which rapid reorganisation of blood circulation is mandatory;
- in veterinary medicine for gain weight increment in animals and for the increase in sperm stability in storage.

The present invention further relates to the use of pentadecapeptide salts of the present invention for the preparation of formulations for use as food supplement.

DETAILED DESCRIPTION OF THE INVENTION

The composition and structure of the new compounds was determined by the use of a mass spectrometer, by amino acid analysis, $^1$H-NMR, FTIR and UV spectra. UV spectra were recorded in Varian Carry 50 spectrometer, FTIR spectra in Perkin Elmer 727B spectrometer, mass spectra on AutoSpec Q spectrometer and $^1$H-NMR spectra on Bruker Advance DPX500 spectrometer. Specific optical rotation $[\alpha]_D^{28}$ was determined with Perkin Elmer type 141 spectrometer. For optical imaging in Example 43 camera Veho Discovery VMS-001, x30-30 was used, for thermographic imaging infrared camera T-335 (FLIR, USA) with FLIR QuickPlot software was used.

The above-mentioned problem was solved by the new salts of pentadecapeptide bepecin with basic amino acids which can be in L-, D-, or DL-form. Typical amino acids are arginine, lysine, ornithine, 2,4-diaminobutyric acid, 2,6-diaminocapronic acid, 2,6-diaminohexanoic acid, 2,5-diaminopentanoic acid, 2,6-diaminopimelic acid, 2,3-diaminopropionic acid, citruline, homoarginine, homolysine and similar. These salts can consist of one molecule of pentadecapeptide and one, two or three molecules of a basic amino acid.

The pH value of salt solutions depends on the salt composition which mediates salt stability. Salts with L-arginine are preferably used. They are generally prepared by reacting pentadecapeptide (SEQ ID NO: 1) with basic amino acids in molar ratios ranging from 1:1 to 1:3 (pentadecapeptide:basic amino acid) in a water solution. First, an amino acid is added in excess, then follows retitration of the excess with a diluted acetic acid to adjust the appropriate pH value. Optimal pH values are: in salts with a molar ratio 1:1 (pentadecapeptide:BAA) from 4.1 to 5.0, preferably 4.60±0.05, in salts with a molar ratio 1:2 from 6.7 to 7.8, preferably 7.40±0.05, in salts with a ratio 1:3 this value is not adjusted. The salt solutions are then purified on a HPLC column, filled with a reverse phase sorbent. After freeze-drying of the corresponding efflux pentadecapeptide salts of high purity are obtained.

The obtained salts are very well soluble in water. Pentadecapeptide salts containing 2 mols of basic amino acids per 1 mol of pentadecapeptide have the most favourable properties, preferred is bepecin di-L-arginine salt (abbr.: Arg-BPC).

A starting compound for the synthesis, pentadecapeptide BPC-157 or bepecin, is prepared with a peptide synthesis on a solid, polymeric carrier as described in previous patents EP 0572688, U.S. Pat. No. 6,268,346 and in publication Z. Pflaum, R. Ručman, Acta Chem. Slov., 2005, 52, 34-39. Pentadecapeptide can be in a free form, as ammonium or sodium salt, or even in the form of acetate or trifluoroacetate.

The stability of bepecin di-L-arginine salt (1:2, abbr. Arg-BPC) at an increased temperature was determined by an accelerated ageing method at 50° C. and relative humidity of 65%, which represents relatively very stringent conditions for a compound having a peptide structure.

TABLE 1

Pentadecapeptide content decrement in standing at 50° C. and relat. humidity 65%:

| Substance: | 0 day | 10 days | 30 days | 60 days | 90 days |
|---|---|---|---|---|---|
| BPC acetate | 99.65% | 95.97% | 91.98% | 85.49% | 85.90% |
| BPC Na salt | 99.20% | 97.22% | 96.46% | 97.38% | 97.14% |
| Arg-BPC | 99.46% | 99.29% | 99.20% | 98.96% | 99.07% |
| Arg-BPC/ NaHCO₃ | 99.46% | 99.37% | 99.29% | 99.16% | 99.15% |
| Lys-BPC | 99.47% | 99.24% | 99.27% | 98.90% | 99.28% |

The table further shows that the addition of sodium hydrogen carbonate to bepecin salt increases its stability at an increased temperature. This addition will be in the range from 0.5 mg to 3.0 mg per 1 mg of bepecin. This property will be taken into account in the composition of tablets and capsules. A separate experiment with an addition of special sugars, e.g. trehalose or D-mannitol, shows similar improvement of stability. The stability of bepecin salt with L-arginine in water solutions was determined after incubation of aqueous salt solutions in concentration 1 g/100 ml, at 50° C., and in a separate test in very stringent conditions: at 100° C., where the decomposition was determined after one hour.

TABLE 2

Pentadecapeptide content decrement in water at 50° C./time (hours):

| Substance: | pH | start/0 | 20 | 65 | 148 | 388 |
|---|---|---|---|---|---|---|
| BPC acetate | 3.88 | 98.89% | 71.17% | 55.25% | 52.55% | 21.30% |
| BPC Na-salt | 8.42 | 99.01% | 98.36% | 97.47% | N.D. | 96.74% |
| Arg-BPC | 7.35 | 99.05% | 98.97% | 99.04% | 99.10% | 99.01% |
| Lys-BPC | 7.28 | 99.07% | 99.40% | 99.09% | 99.35% | 99.01% |
| Orn-BPC | 7.12 | 100.00% | 99.64% | 99.78% | 99.59% | 99.44% |

TABLE 3

Pentadecapeptide content decrement in water at 100° C. - 1 hour:

| Substance: | start | after 1 hour |
|---|---|---|
| BPC acetate | 98.89% | 56.80% |
| BPC Na-salt | 99.01% | 98.56% |
| Arg-BPC | 99.05% | 99.08% (unchanged!) |

Stability of a compound in gastric juice is an important parameter, particularly in peptides, which very rapidly decompose in the presence of pepsine enzyme and in an acidic medium. Better stability in gastric juice means a longer period, in which the compound is available for resorption and its therapeutical activity.

Artificial gastric juice illustrates the conditions in normal human gastric juice and contains: 0.08 mol of hydrochloric acid, 0.03 mol of sodium chloride and 1.0 g of pepsin in 1000 ml of water.

The studied peptide salt in concentration 10 mg/5 ml was incubated in artificial gastric juice with pH values 2.0, 3.0 and 4.0 at 37° C.

TABLE 4

Pentadecapeptide content decrement (rel. %) in gastric juice at pH = 2.0

| Substance: | Time (hours): | | | | | |
|---|---|---|---|---|---|---|
| | 0 | 0.5 | 1.0 | 1.5 | 2.0 | 2.5 |
| BPC acetate | 100 | 21.4 | 8.2 | 4.75 | 2.46 | 2.1 |
| BPC Na-salt | 100 | 21.6 | 6.7 | 4.4 | 4.2 | 2.7 |
| Arg-BPC | 100 | 30.2 | 13.5 | 8.2 | 6.0 | 4.9 |

TABLE 5

Pentadecapeptide content decrement (rel. %) in gastric juice at pH = 3.0

| Sub-stance: | Time (hours): | | | | | | |
|---|---|---|---|---|---|---|---|
| | 0 | 0.5 | 1.0 | 2.0 | 3.0 | 4.0 | 5.0 |
| BPC acetate | 100 | 41.7 | 26.1 | 7.8 | 2.5 | 1.1 | 0.08 |
| BPC Na-salt | 100 | 81.9 | 71.6 | 56.0 | 40.2 | 29.7 | 10.1 |
| Arg-BPC | 100 | 98.1 | 96.5 | 93.6 | 90.0 | 87.2 | 84.9 |

TABLE 6

Pentadecapeptide content decrement (rel. %) in gastric juice at pH = 4.0

| Sub-stance: | Time (hours): | | | | | | | | |
|---|---|---|---|---|---|---|---|---|---|
| | 0 | 1 | 2 | 3 | 4 | 5 | 6 | 7 | 8 |
| BPC acetate | 100 | 89.7 | 81.3 | 72.5 | 60.9 | 56.4 | 48.8 | 44.6 | 38.0 |
| BPC Na-salt | 100 | 99.0 | 98.9 | 94.6 | 89.7 | 78.3 | 76.3 | 68.2 | 60.9 |
| Arg-BPC | 100 | 99.9 | 99.5 | 98.7 | 96.1 | 89.8 | 84.6 | 73.5 | 67.2 |

The content of pentadecapeptide BPC-157 in tested samples was determined by HPLC method in the following system:
  column: Reprosil Orpegen C18, 100, 5 μm, 250×4.6 mm,
  mob. phase A: 0.1% trifluoroacetic acid/5% acetonitrile/water
  mob. phase B: 0.11% trifluoroacetic acid/40% acetonitrile/water
  gradient: from 100% A to 30% A in 25 min
  temperature: 20° C.
  flow: 1.5 ml/min
  detection: UV, 210 nm The results of stability determination show that bepecin salts with basic amino acids are substantially more stable than other hitherto known salts of pentadecapeptide in question, which is surprisingly a huge advantage. In any case these new salts are better than bepecin salts with different amines, alkali and earth alkali metals according to patents EP 0983300 and U.S. Pat. No. 6,288,028, which are prone to formation of polar degradation product (up to 10%, structure not yet defined). A consequence of better stability is also better biological activity, since the intact compound is present in an organism for a longer period of time and available for more efficient resorption.

Stability in Light

Compounds of such type are very susceptible to ultraviolet light. An aqueous solution of Arg-BPC (1 g/100 ml of water) at 20° C. was radiated with ultraviolet light of a wavelength of 253.7 nm and absorption was measured within wavelength range from 230 to 350 nm over a period of 70 min every 10 min. The results are represented in FIG. 1 and confirm that the compound is stable.

The new salts of bepecin which are the object of the present invention can be used as a therapeutically active substance which is converted together with an inert pharmaceutically acceptable carrier into a suitable form such as tablets and capsules used for the treatment of diseases and conditions, organism injuries, wounds, bone fractures and burns as well as viral infections, as determined by pharmacological studies before.

An object of the invention is also an oral pharmaceutical formulation containing an amino acid salt of bepecin salts, to which different additives are admixed. Pharmaceutically acceptable additives that are used are substances generally well known to one skilled in the art. Inert substances or pharmaceutical additives are selected from the following groups:
  fillers such as: anhydrous lactose, microcrystalline cellulose, starch, calcium phosphate, calcium carbonate, maltodextrin, D-mannitol, trehalose and others;
  binders such as: microcrystalline cellulose, hydroxyalkyl celluloses, povidone, cellulose esters, starch or a mixture thereof;
  disintegrants such as: starch, crosslinked sodium croscarmelose, crospovidone, microcrystalline cellulose, sodium carboxymethyl cellulose and others, mostly in an amount of 1-10%;
  stabilizers such as: alkali metal and alkaline earth metal hydrogen carbonates or selected sugars, preferably sodium hydrogen carbonate and D-mannitol;
  lubricants and glidants used in tableting: talc, magnesium stearate, stearic acid, potassium stearate and colloidal silica. These substances are usually added to other ingredients in the final phase.

A comparison of the stability of bepecin salts in solutions having different acidity shows that the compound is the most stable in a slightly acidic, neutral or even slightly alkaline medium, preferably in a pH range from 6.5 to 8.5. Reasonably, this should be taken into account in composing pharmaceutical formulations. In the preparation of granulates for tableting and capsulating it is suitable to add slightly alkaline substances such as alkali metal and alkaline earth metal hydrogen carbonates and carbonates, basic carbonates and oxides such as sodium hydrogen carbonate, calcium hydrogen carbonate and magnesium oxide, which improve stability. Addition of selected sugars prevents the Maillard reaction.

Pharmaceutical formulations are prepared by known processes such as direct mixing, dry granulation, wet granulation, or by spraying of a bepecin salt solution onto inert pharmaceutical substances under simultaneous drying in a counterflow of warm air. To the granulate thus obtained other ingredients are added, if necessary, homogenized and tableted or capsulated in a conventional manner. In a final phase, tablets, capsules or lozenges can be coated with a protective film resistant to gastric juice activity, so that bepecin releases not earlier than in the intestines.

The amino acid component in the present new salt is a reason for greater hydrophobicity of the active substance in this form. It is therefore realistic to expect a better transfer through biological membranes, which also provides for a manufacture of a transdermal preparation—such as cream, ointment or patch.

Transdermal system consists of an active substance-impermeable backing layer, a pressure sensitive polymer layer serving as a reservoir for the active substance, a protective foil that is perforated in several places to allow penetration of the active substance therethrough, and an outer protective foil.

Bepecin salt can be used in the form of a solution, enema, injection or dry injection as well. In this case an aqueous solution of a buffer with an optimal pH value between 6 and 8, preferably between 7.0 and 7.5 is used as a solvent. The solution can be sterilized by fine filtration through a filter with 0.22 μm pores or by very short heating to 100° C. A dry injection is prepared in a way that a sterile solution containing bepecin salt, buffer and preservative is frozen in ampules and lyophilized.

A solution intended for ocular or nasal drops is prepared by using an isotonic and isohydric solution with a pH value ranging from 7.0 to 7.5, which in addition to the active substance bepecin also contains a buffer and a preservative and is filtered in sterile conditions. Suppositories for rectal and vaginal use are prepared by taking gelatine, cocoa butter, natural or semisynthetic fats having a low melting point, paraffin, glycerine, polyethylene glycols with a molecular weight from 1000 to 6000 for a base, into which an aqueous solution of bepecin is admixed. Additionally, emulsifiers, antioxidants and preservatives are added.

Bepecin salts can also be used in the form of a cream, ointment or gel. In this case a lipophilic, hydrophilic or amphyphilic fat base based on natural, vegetal or animal fats and natural oils is used, to which base also preservatives, colourings, emulsifiers, water or buffer solutions and antioxidants are added.

Bepecin is a compound which acts at very low doses. Therapeutic doses for oral use will range from $10^{-5}$ to $10^{-2}$ mg/kg of body weight, depending on the type and severity of the disease. A common dose in tablets, lozenges or capsules will range from 0.1 to at most 5 mg. Concentrations in local use are higher ranging from 0.001% to 0.5%. Determination of optimal dose is subject to assessment and experience. It is very important that bepecin does not show any side effects or toxicity. Based on the above and its numerous favourable effects on an organism there is also a possibility of its use in the form of a food supplement at very low doses ranging from 1 μg to at most 0.1 mg daily. In formulations prepared for this purpose it can also be combined with vitamins, minerals and other favourably acting substances.

According to the invention, other single active substances, which improve the principal activity of bepecin or act synergistically can be also added. These are substances from the following groups:

substances with an antibiotic activity such as gentamicin, azythromycin, ampicillin, cephalosporins and doxycycline, particularly in formulations for local use, wherein it is desired that both antiviral and antibiotic activities are reached simultaneously. Such examples are tick bites, in which the intention is twofold: to prevent borellia and tick-borne encephalitis simultaneously;

substances with an antioxidant activity, such as dry green tea extract, coenzyme $Q_{10}$, idebenon, curcumin, abigenol, pycnogenol and others.

A combination with coenzyme $Q_{10}$ or ubiquinone is of special interest. Coenzyme $Q_{10}$ is a very efficient antioxidant and a free radical scavenger and can additionally be used in heart diseases associated with a decreased blood flow, hypertension and at signs of heart insufficiency. Lately, it has proved that an important antioxidant is also curcumin which has a powerful anticarcinogenic activity.

Our research has demonstrated a very favourable activity of new bepecin salts in the therapy of neurological diseases, e.g. multiple sclerosis. This inflammatory disease causes damage to the myelin sheaths around the axons in the brain and spinal cord. Nerve cells usually communicate by sending electrical signals through nerve fibres-axons, where myelin sheaths are insulators. In the case of myelin sheath damage the conduction of electrical signals is interrupted or very disturbed. In multiple sclerosis the body immune system attacks and injuries the myelin sheaths. There is no known effective cure against multiple sclerosis. The existing therapy is aimed at improving the functions after attacks, preventing new attacks, but usually has adverse effects or is poorly tolerated.

Bepecin has antiimflammatory, reparative, protective and immunomodulatory activity. On the basis of pharmacological research a good therapeutic effect of bepecin on multiple sclerosis is anticipated. The use of a formulation with bepencin-L-arginine salt could be useful in the adjuvant treatment of secondary injuries and disturbances caused by infections with Lyme borreliosis (L. Reik et all., Neurology, 46, 1989, 790-795) or syphilis (D. Grey, The Lancet, Jul. 12, 1986, 75-77). In all these cases myelin sheaths are injured and lesions in brain are visible with MRI.

Multiple sclerosis will be treated by oral preparations containing salts of bepecin in a stabilized form at doses from 1 mg to 5 mg. No adverse or unpleasant side effects are connected with use of bepecin preparations and they are safe for long term application as well.

On the basis of pharmacological experiments on animals we believe that the use of bepecin salts with basic amino acids in the form of suitable pharmaceutical preparations will be of benefit also in other neurological diseases, such as neuropathy, myasthenia gravis and others.

Bepecin has also a very beneficial effect on reorganisation of collateral blood vessels after a severe injury of femoral arteries.

The present invention is further illustrated, but not limited, by the following examples intended to clarify the process. Examples from 18 to 44 describe experiments carried out to determine the pharmacological activity of bepecin. They have been performed by using different in vitro and in vivo experimental models widely used in practice and by citation of literature sources. Bepecin was in all experiments used in the form of a salt with L-arginine.

BRIEF DESCRIPTION OF FIGURES

FIG. 3 Illustration of the effect of bepecin to tick-borne encephalitis virus (TBE):
  A: Simultaneous application of $10^2$ of TBE virus (i.c.v.) and saline 0.9% NaCl (i.p.) without bepecin.
  B: Simultaneous application of $10^2$ of TBE virus (i.c.v.) and bepecin 10 μg/kg (i.p.) Infection symptoms occur at a considerably later stage.
  C: Application of bepecin 10 μg/kg (i.p.) 4 hours before infection with $10^2$ of TBE virus (i.c.v.). No clinical signs of disease Animals were euthanized after 30 days and part of brain homogenisate was transferred to a new animal; see: D.
  D: Simultaneous application of brain homogenisate and a new infection with $10^2$ of TBE virus (i.c.v.). No signs of disease even after 50 days.

FIG. 4 $^1$H-NMR spectra of bepecin salts, recorded in $D_2O$:
  A: spectrum of bepecin L-lysine salt (1:3),
  B: spectrum of bepecin L-arginine salt (1:2),
  C: spectrum of bepecin L-ornithine salt (1:2).

Figure 1:
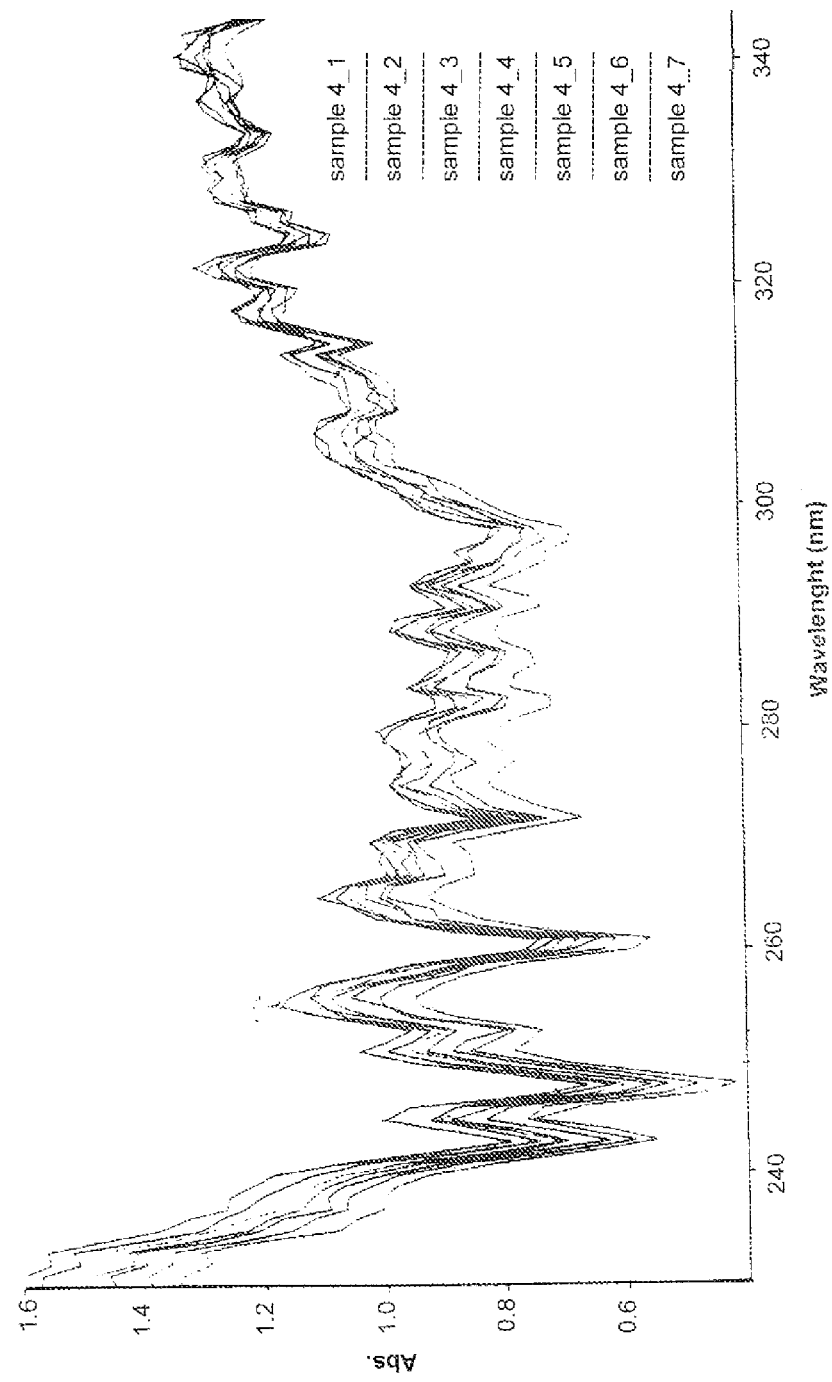
FIG. 1 Illustration of stability of a bepecin solution when irradiated by ultraviolet light; absorptions of samples 1 to 7 were measured each 10 min.

B: a test group was subject to bepecin bath for 1 min—abundant collateral vascular vessels are visible with full interconnections.

EXAMPLES

Example 1. Preparation of Bepecin D-Arginine Salt (1:2)

Bepecin trifluoroacetate (500 mg, 0.34 mmol) was dissolved in 25 ml of water. While moderately stirring, D-arginine (212 mg, 1.22 mmol) was gradually added and stirred for further 15 min. The pH value of the solution was then adjusted to 7.40±0.05 by diluted acetic acid (50%) The solution was clear filtered and freeze dried. The lyophilisate was dissolved in a small volume of water and applied on a start of the HPLC column (ID=2.2 cm, h=25 cm, sorbent Reprosil C18, 10 μm) previously washed and equilibrated with pure water. Elution with an increased concentration of isopropanol in water: in 30 min from 0 to 5% of isopropanol. First fractions containing salts and impurities were discarded. The collected main fraction was freeze dried. 550 mg of a dry salt were obtained that contained two mol of D-arginine/1 mol of pentadecapeptide.

An amino acid analysis corresponds to the composition:
2-Ala, 1-Val, 3-Gly, 4-Pro, 1-Leu, 2-Asp, 1-Glu, 1-Lys, 2-Arg.
MS (TOF MS ES+): $M_1$=1419.8 (pentadecapeptide+$H^+$) $M_2$=175.1 (D-arginine+$H^+$)
FTIR $\nu$ ($cm^{-1}$): 3275, 3057, 2958, 2872, 1628, 1533, 1448, 1394, 1315, 1244, 1204, 1161, 1096, 1044, 919, 875.
Specific optical rotation (c=1 g/100 ml) $[\alpha]_D^{28}$=−154°.
HPLC purity: 99.48%.

Example 2. Preparation of Bepecin L-Arginine Salt (1:1)

A solution with bepecin acetate and L-arginine was prepared as described in Example 1. The pH value of the solution was adjusted to 4.60±0.05 with a diluted acetic acid (50%) and the obtained solution was treated like in Example 1. 232 mg of an amorphous powder was obtained which contained 1 mol of L-arginine per 1 mol of bepecin.

An amino acid analysis corresponds to the composition:
2-Ala, 1-Val, 3-Gly, 4-Pro, 1-Leu, 2-Asp, 1-Glu, 1-Lys, 1-Arg.
MS (TOF MS ES+): $M_1$=1419.8 (pentadecapeptide+H) $M_2$=175.1 (L-arginine+H)
FTIR $\nu$ ($cm^{-1}$): 3265, 3060, 2960, 2875, 1629 (CONH), 1534, 1448, 1394, 1312, 1243, 1202, 1160, 1043, 919, 873.
Specific optical rotation (c=1 g/100 ml) $[\alpha]_D^{28}$=−119.0°.
HPLC purity: 98.57%.

Example 3. Preparation of bepecin L-arginine salt (1:2), (abbr. Arg-BPC)

Bepecin acetate (1 g, 0.705 mmol) and L-arginine (420 mg, 2.41 mmol) were dissolved in 4 ml of water (pH value of the solution was 8.92) and stirred 20 min. The pH value was then adjusted to 7.40±0.05 with a diluted acetic acid (50%). This solution was applied on a start of the HPLC column (ID=2.2 cm, h=25 cm, sorbent: Reprosil C18, 10 μm) previously well washed and equilibrated with pure water. It was eluted gradually with an increasing concentration of isopropanol in water: in 30 min from 0 to 5% of isopropanol. Fractions containing salts and impurities were discarded. The main fraction was freeze-dried. 1.10 g of a white amorphous powder, easily soluble in water was obtained. An amino acid analysis corresponds to the composition:
2-Ala, 1-Val, 3-Gly, 4-Pro, 1-Leu, 2-Asp, 1-Glu, 1-Lys, 2-Arg.
MS (TOF MS ES+): $M_1$=1419.8 (pentadecapeptide+$H^+$) $M_2$=175.1 (L-arginine+$H^+$)
FTIR $\nu$ ($cm^{-1}$): 3271, 3057, 2958, 2875, 1632 (CONH), 1539, 1448, 1394, 1244, 1205, 1161, 1097, 1044, 919, 873, 652.
Spec. optical rotation (c=1 g/100 ml) $[\alpha]_D^{28}$=−124.3°.
HPLC purity: 99.54%.
$^1$H-NMR spectrum is illustrated in FIG. 4/B.

Example 4. Preparation of Bepecin L-Lysine Salt (1:3), (Abbr. Lys-BPC)

Bepecin acetat (500 mg, 0.34 mmol) and L-lysine (176 mg, 1.2 mmol) were dissolved in 3 ml of water and stirred for 20 min. The solution was applied onto a HPLC column and purified as described in Example 3. 283 mg of a white amorphous powder, easily soluble in water were obtained.
An amino acid analysis corresponds to the composition:
2-Ala, 1-Val, 3-Gly, 4-Pro, 1-Leu, 2-Asp, 1-Glu, 4-Lys
MS (TOF MS ES+): $M_1$=1419.8 (pentadecapeptide+$H^+$) $M_2$=147.1 (L-lysine+$H^+$)
FTIR $\nu$ ($cm^{-1}$): 3269, 3060, 2958, 2875, 1981, 1627 (CONH), 1532, 1447, 1393, 1315, 1241, 1203, 1160, 1008, 919, 873, 654.
Specific optical rotation (c=1 g/100 ml) $[\alpha]_D^{28}$=−130°.
HPLC purity: 99.47%.
$^1$H-NMR spectrum is illustrated in FIG. 4/A.

Example 5. Preparation of Bepecin L-Ornithine Salt (1:2), (Abbr. Orn-BPC)

Bepecin acetat (500 mg, 0.34 mmol) and L-ornithine (1.77 mg, 1.05 mmol) were dissolved in 5 ml of water and the pH value was adjusted to 7.40±0.05 with a diluted acetic acid. This solution was purified on a HPLC column as described in the previous example. 412 mg of a white amorphous powder, easily soluble in water were obtained.
An amino acid analysis corresponds to the composition:
2-Ala, 1-Val, 3-Gly, 4-Pro, 1-Leu, 2-Asp, 1-Glu, 1-Lys, 2-Orn
MS (TOF MS ES+): $M_1$=1419.8 (pentadecapeptide+$H^+$) $M_2$=170.1 (L-Ornithine+$H^+$)
FTIR $\nu$ ($cm^{-1}$): 3269, 2958, 2875, 2162, 1636 (CONH), 1522, 1442, 1389, 1311, 1243, 1203, 1160, 1094, 1040, 911, 873, 654, 610
Specific optical rotation (c=1 g/100 ml) $[\alpha]_D^{28}$=−137°.
HPLC purity: 99.30%.
$^1$H-NMR spectrum is illustrated in FIG. 4/C.

Example 6. Tablets

| Ingredient: | mg/tablet |
| --- | --- |
| Arg-BPC | 1.00 |
| Cellulose Avicel | 20.04 |
| Anhydrous lactose | 60.53 |
| Sodium hydrogen carbonate | 2.25 |
| Crospovidone | 5.25 |
| Colloidal silica | 0.33 |
| Magnesium stearate | 0.60 |
| | 90.00 mg |

Example 7. Tablets—Film Coated

| Ingredient: | mg/tablet |
|---|---|
| Arg-BPC | 2.00 |
| Trehalose | 96.20 |
| Hydroxypropylcellulose | 11.20 |
| Sodium hydrogen carbonate | 2.60 |
| Curcumin | 5.00 |
| Croscarmellose sodium | 2.00 |
| Magnesium stearate | 1.20 |
| Enteric coating: | |
| Eudragit S100 | 0.48 |
| Ammonium hydroxide, 1 mol/l | 0.25 |
| Triethylcitrate | 0.24 |
| Talc | 0.16 |
| Water | 2.90 |

Example 8. Eye Drops

| Ingredient: | |
|---|---|
| Arg-BPC | 0.50 mg |
| Sodium phosphate buffer 0.05 mol/l, pH 7.4 | 85 ml |
| Sodium chloride | 0.44 g |
| Benzyl alcohol | 0.20 ml |
| Water ad. | 100 ml |

Example 9. Capsules

| Ingredient: | mg/capsule |
|---|---|
| Lys-BPC | 1.0 |
| Sodium hydrogen carbonate | 2.5 |
| Lactose monohydrate | 80.6 |
| Pregelatinized corn starch | 15.4 |
| Magnesium stearate | 0.5 |
| | 100 mg |

Example 10. Solution for Local Use

| Ingredient: | g/100 ml |
|---|---|
| Injection water | 20.00 |
| Arg-BPC | 0.05 |
| Glycerol | 22.00 |
| Benzalkonium chloride | 0.02 |
| Sodium phosphate buffer, 0.05 mol/l, pH 6.5 | ad 100 ml |

Example 11. Gel

| Ingredient: | g/100 g |
|---|---|
| Injection water | 70.00 |
| Arg-BPC | 0.20 |
| Carbopol 974, Noveon ® | 1.00 |
| Methyl-p-hydroxybenzoate | 0.18 |
| Propyl-p-hydroxybenzoate | 0.02 |
| Sodium hydroxide 0.01 mol/l for adjustment of pH value to 7.0 | |
| Injection water ad.: | total 100 ml |

Example 12. Cream

Lipophilic ingredients for 100 g of cream: stearic acid, cetearyl and stearyl alcohol, saturated medium chain triglycerides with caprylic and capric acid, silicone oil Dimeticon and sodium cetearyl sulphate totalling 16.4 g were melted at 60° C. Hydrophilic ingredients: to the sterile filtered pure water (70 g) propylene glycol (3 g) and the preservative butyl-4-hydroxybenzoate (0.5 g) were added, it was stirred and heated to 60° C. The pH value was adjusted to 6.5 by using a 0.1 molar sodium hydroxide solution. Thereafter, the hydrophilic phase was added under stirring to the lipophilic phase, cooled and stirred until 30-35° C. was reached. The antioxidant tocopherol acetate (0.05 g) was added to this mixture, well stirred and finally 10 g of an aqueous solution containing Arg-BPC (0.1 g) was added. The mixture was well stirred and filled into appropriate containers.

Example 13. Suppositories

| Ingredient: | mg/suppository |
|---|---|
| Arg-BPC | 0.5 |
| Water | 25.0 |
| Glycerol | 30.5 |
| Cocoa butter | 180.0 |
| Methyl-p-hydroxybenzoate | 2.0 |
| Polyethylene glycol PEG 1000 | 61.0 |
| Tocopherol | 1.0 |
| | 300 mg |

Example 14. Orodispersible Tablets

| Ingredient: | mg/tablet |
|---|---|
| Arg-BPC | 0.5 |
| StarLac ® | 48.9 |
| Acesulfame K | 0.4 |
| Magnesium stearate | 0.1 |
| Colloidal silica | 0.1 |
| | 50.0 mg |

Example 15. Transdermal Preparation—Patch

Active ingredients: Arg-BPC (5.0 mg) and doxocycline (1.0 g) were dissolved in a mixture of water (10 g), diethyleneglycol monoethyl ether (1.8 g), polyethylene glycol monolaurate (0.5 g) and diethanolamine (0.2 g). 25 g of the polymer solution GEL VA. RTM. 2484 (Monsanto) were added and well stirred. The solution was then left to stand for 20 min to deaerate. It was then applied onto an impermeable membrane (polyethylene film or aluminized polyethylene film) such as 3M-Scotchpack 1006) and dried at 40-50° C. This layer was then covered with a porous controlled substance release foil and a protective foil and cut to a suitable size.

Example 16. Tablets with Prolonged Stability

Preformulation:

Bepecin L-arginine salt 1:2(1.0 g) and D-mannitol (1.0 g) were dissolved in 20 ml of water, sterile filtered (0.22 μm filter) and freeze-dried. The obtained white amorphous powder contains 50% of bepecin salt.

Preparation of Tablets:

| Ingredient: | mg/tablet |
|---|---|
| Preformulated Arg-BPC (50%) | 2.0 |
| D-mannitol pharm. grade (Pearlitol 300DC) | 70.0 |
| Cellulose Avicel (PH 102) | 60.6 |
| Sodium hydrogen carbonate | 1.3 |
| Colloidal silica (Aerosil 200) | 0.7 |
| Magnesium stearate | 1.0 |
| | 100 mg |

Stability Test:

Tablets prepared according to described process were incubated at −15° C., +25° C. and +50° C./RH 65% and an assay of bepecin was measured with HPLC method. Duration of incubation: 18 months.

| | Temperature: | | |
|---|---|---|---|
| | −15° C. | +25° C. | +50° C. |
| Assay (HPLC) of bepecin: | 99.8% | 96.6% | 92.35% |

If an extrapolation method is used, it can be concluded that prepared tablets will be stable at room temperature at least 2 years.

Example 17. Food Supplement with Bepecin—Effervescent Tablets

| Ingredient: | mg/tablet |
|---|---|
| Bepecin salt | 0.5 |
| Glucose | 150.0 |
| Fructose | 29.0 |
| Vitamin C | 50.0 |
| Sodium hydrogen carbonate | 30.0 |
| Natural aroma | 0.5 |
| | 260 mg |

Example 18. Activity of Bepecin on NO-System

Nitric oxide (NO) has a role of a signalling molecule in endothelial and nerve cells and also of the so-called killing molecule which is activated by immune cells. In general, in both excess and deficiency of NO it seems that NO strongly contributes to the formation of different abnormalities and disorders in the organism, such as hypertension, angina, impotence, circulatory and septic shock, heart failures, arrhythmias, stroke, inflammatory processes, adhesion and aggregation of blood platelets and leucocytes, bad healing of wounds and burns, muscle, tendon, ligament and bone injuries, gastrointestinal lesions, diabetes, pancreatitis, circulatory and septic shock, endothelial disorders, heart defects and Parkinson's disease.

Bepecin has a characteristic property to affect the release and normalization of NO-level and to counteract disturbances after the application of NO-blocking substances, such as L-NAME and against the side effects of applications of NO-precursors such as L-arginine. This activity of bepecin to the NO-system clarifies the very wide spectrum of its pharmacological activity to some extent.

By using the methods described in literature: J. Physiol. Paris, 1007, 91, 139-49; Regul. Pept., 2009, 156 (1-3), 83-89; J. Pharm. Sci., 2008, 108 (1), 7-1; J. Clin. Exp. Cardiology, 2012, 3, 201, Regul. Pept. 2013, 181C, 50-66, Med. Sci. Monit. 2006, 12, 36-45 and Eur. J. Pharmacol., 1997, 332 (1), 23-33, we experimentally demonstrated that bepecin may cause "in vitro" NO-release and counteract the effects of L-arginine and L-NAME. It thus normalizes blood pressure disorders, which are consequently caused by NO.

Bepecin also protects against isoprenalina-myocardial infarction, and arrhythmias caused by methyldigoxin (6 mg/kg i.v. or i.p.), when used in a dose range from 10 ng to 10 μg/kg of body weight, parenterally or orally. It prevents aggravation of lesions caused by the NO-blocker L-NAME. Bepecin counteracts disturbances caused by too high and too low NO-values and re-establishes normal NO-system functions.

Bepecin normally has a modulating effect in the NO-system if used in doses ranging from 10 ng to 10 μg/kg body weight, parenterally or orally. It prevents from aggravation of lesions caused by the NOS-blocker L-NAME.

Example 19. Effect on Wound Healing

By using the methods specifically described in literature: J. Physiol. Pharmacol., 2009, 60 (Suppl. 7), 191-196; J. Orthop. Res., 2010, 28, (9), 1155-1161; Burns, 2005, 31 (3), 310-315; Bone, 1999, 24 (3), 195-202; Surg. Today, 2007, 37 (9), 768-777 we have found that bepecin markedly increases healing of the below indicated diseases due to its improvement of angiogenesis and production of collagen:
  skin incisions;
  deep skin burns;
  various anastomoses as intestinal wounds; diabetic wounds;
  various fistulas;
  various tissue transections, particularly ligament, tendon, muscle and nerve transections;
  bone fractures, including simultaneous soft tissue injuries;
  corneal wounds, even with complete epithelium abrasion or corneal ulcer.

On the basis of these results and a great similarity between the healing processes in rats and humans bepecin will be successfully used in healing wounds, burns and bone fractures in humans.

Example 20. Endothelium Protection, Angiogenesis, Thrombosis and Bleeding Disorders Based on the evidence largely reviewed (J Physiol Paris. 1993; 87, 313-27, Inflammopharmacol 2006; 14, 214-21, Curr Pharm Des 2010; 16, 1224-34, J. Physiol. Pharmacol., 2009, Dec., 60, Suppl7, 161-5, Thromb. Res., 2012, May, 129 (5), 652-9; we evidenced that bepecin influences the activities after vascular integrity loss. Bepecin rescues endothelium integrity maintenance following absolute alcohol intragastric instillation (i.e. it exhibits a cytoprotective effect), and also, bepecin exhibits a rapid wound healing effect in both gastrointestinal and extra-gastrointestinal tissue lesions. We consequently demonstrated that after abdominal aorta anastomosis in rats, bepecin application prevents obstructive thrombus formation, at least for 24 h, and when given in the presence of already formed thrombosis and vascular obstruction, rapidly destroys already formed obstructing thrombus along with the rescuing of lower leg function. In other experiments carried out in rats, after amputation, we demonstrated that bepecin consistently counteracts prolonged bleeding and thrombocytopenias, but also aspirin-, warfarin- and heparin-prolonged bleeding. Bepecin was administered intraperitoneally, intravenously or intragastrically (10 µg/kg, 10 ng/kg body weight).

An important finding in preventing and eliminating an already formed clot, prolonged bleeding and thrombocytopenias caused by aspirin-, warfarin- and heparin-prolonged bleeding as well as thrombocytopenias caused by huge doses of heparin (250 mg/kg, 25 mg/kg, 10 mg/kg i.v.), warfarin (1.5 mg/kg i.g. once daily for 3 consecutive days), aspirin (0.1 g/kg i.g. (once daily/3 consecutive days or 1.0 g/kg i.p. once) was that bepecin does not affect the coagulation parameters by itself Consequently, a therapy with bepecin may be extended to all relevant conditions where either thrombosis or blood disorders are present. Bepecin may also be an original therapy in conditions where the function of egr-1 and/or naB2 is impaired.

Example 21. Adhesion Formation

Our previous research demonstrated a distinctive effect of bepecin on inflammation processes and their consequences. In addition, we also demonstrated a therapeutic effect of bepecin against the adhesion formation (sticking) and protection against development of adhesions (or at least considerable reduction).

By several suitable methods (i.e. a surgical excision of parietal peritoneum in rats according to the methods described in Gastroenterology, 2010, 138, (5, Suppl. 1) 753; ileo-ileal anastomosis according to Surg. Today, 2007, 37 (9), 768-777; jejuno-ileal anastomosis according to Dig. Dis. Sci., 2009, 54 (10), 2070-2083), we have shown that bepecin in general reduces formation of adhesions (both macroscopically and microscopically) associated with functional improvements (i.e. anastomosis strengthening, animal weight gain to the normal level). Bepecin was used in its regular low doses range from 10 ng to 10 µg/kg body weight parenterally, orally or locally.

Considering the existing congruence between the animal models and conditions in a human organism, we claim therapeutic use of bepecin in these disorders.

Example 22. Immunomodulation

Immunomodulation (particularly as a vital macrophage function) induced by natural or synthetic substances is considered as a good alternative to the prevention and treatment of both infectious and neoplastic diseases.

By using the method described in J. Physiol. Pharmacol., 2009, 60, Suppl. 2, 69, "in vivo" efficacy of bepecin to increase the activity of macrophages as major immunologically active cells in mice (i.e. increased macrophage mobility, restoration of M/P ratio between mononuclear and polynuclear leukocytes) was determined. Mice were injected daily with a dose of 50 µg or 100 µg/kg per body weight (i.p.) of bepecin for 3 consecutive days. Activated macrophages induced a production and release of factors regulating the function of B-, T- and NK-cells, which is important for immunomodulatory action. This immunomodulatory action of bepecin will be advantageously used as an aid in the therapy of several infectious and neoplastic diseases.

Example 23. NSAIDs—Nonsteroidal Anti-Inflammatory Drugs

As already found, bepecin has a strong action against all inflammatory parameters and simultaneously considerably improves treatment and prevents lesions and injuries, particularly after the use of NSAIDs. Paracetamol, aspirin, diclofenac, ibuprofen, and indomethacin induce numerous side effects described in literature: J. Physiol. Pharmacol., 2010, 61(2), 241-250; Gastroenterology, 2010, 138, 5, Suppl. 1, S-369. This is particularly evidenced by formation of gastric, intestinal, liver and brain lesions, prolonged bleeding and various behavioural disturbances (including convulsions). These were all counteracted by bepecin application either parenteral or oral.

Besides increased bleeding, bepecin also effectively antagonizes thrombocytopenia after the use of aspirin (1g/kg, i.p.) or diclofenac (12.5 mg body weight/kg, i.p.), yet in very low doses ranging from 10 ng to 10 µg/kg of body weight, administered parenterally, intragastrically or in potable water.

Bepecin counteracts the side effects of NSAIDs. Furthermore, considering its beneficial effects on acute and chronic inflammation (wherein also NSAIDs are used) the best way would be to use bepecin alone without NSAIDs.

Example 24. Anaphylaxis and Anaphylactoid Reaction

When given parenterally egg white and dextran induce a severe anaphylactoid reaction in rats (B. N. Halpern, Histamine, Ciba Found. Symp., J. and A. Churchill Ltd, London, 1956, 92-123 and H. Selye, Endocrinology, 1937, 21, 169). Natural and synthetic polymers can induce a massive endogenous histamine release. Anesthetized animals received intravenous solutions of dextrane in concentrations of 6%, 10%, 20%, 40%, 60%, 80%, 90% and/or a solution of an egg white (1 ml/rat or 0.15 ml/mouse) into their tails. Prominent edema appeared on the face, the upper and lower lips, snout, paws and scrotum (presented with extreme cyanosis). The animals experienced poor respiration and several cases of fatalities after dextran and/or egg white application. Contrary, bepecin in regimens (10 µg, 1 µg, 10 ng, 10 pg/kg) effectively both prevents anaphylactoid reactions and vascular collapse and also markedly improves the action of antihistaminic agents such as clomipramine (20 mg/kg) and cimetidine (10 mg/kg), which alone were only poorly effective or even ineffective.

Thus, considering the fact that the used models are regular models fairy mimicking human anaphylactoid reaction, bepecin's beneficial effect in anaphylactic conditions is provided.

Example 25. Corticosteroids

Corticosteroids, particularly given systemically, may result in severe disturbances (i.e. immunosuppression, poor wound healing, etc.). By using the method described in literature: Med. Sci. Monit., 2010, 16 (3), BR 81-88; and Burns, 2005, 31 (3), 310-315 it was found that bepecin completely counteracts corticosteroid-failed wound healing (i.e. 6-alpha-methylprednisolone, 1 mg and 10 mg/kg body weight, i. p. in mice and rats), an effect consistently demonstrated in systemic corticosteroid-treated muscle crush injury, deep skin burns, transected Achilles' tendon or medial collateral ligament, various fistulas, stomach, colon and skin defects or corticosteroid immunosuppression (examination of spleen cells). Bepecin was used in a dose range from 10 ng to 10 μg/kg body weight, parenterally, orally or locally, as a thin layer of a cream (i.e. 1 μg/g of neutral cream).

Thus, presenting the considerable overlap with human circumstances, bepecin could be used in eliminating disorders induced by the use of corticosteroids and/or in some indications even instead of corticosteroids.

Example 26. Hypertension, Hypotension and Blood Pressure Regulation

Experiments carried out as described in: J. Physiol. Paris, 1993, 87 (5), 313-327 and Eur. J. Pharmacol. 1997, 332 (1), 23-33 demonstrated that bepecin has no effect on blood pressure in normotensive animals, but it could both decrease an increased blood pressure, and increase a decreased blood pressure. Specifically, bepecin decreases the increased blood pressure in hypertensive animals with Goldblatt hypertension with two kidneys—2K1C—or with one kidney—1K1C—; rats fed with either high fructose (80%) or high salt (15%) diet for a prolonged period; rats treated with NOS-blocker L-NAME (5 mg/kg, i.v.); or a huge dose of KCl i.p. Bepecin acts against hypotension, i.e. normalizes blood pressure in rats with chronic heart failure and increased serum endothelin-1 value, doxorubicin-induced hypotension (2.5 mg/kg, i.p. 6 times within 15 days), and also reverse chronic heart failure. Also, bepecin counteracts hypotension in rats treated with NO-precursor L-arginine (100 mg/kg i.v.). Regularly, bepecin was given either prophylactically or therapeutically.

Bepecin in doses from 10 ng to 10 μg/kg, parenterally or orally, caused a considerable decrease in or even disappearance of other lesions and disorders otherwise present in these processes.

In hypovoluemic shock, bepecin recovered blood pressure and prevented otherwise lethal outcome. It may also increase blood volume loss, which might otherwise cause death.

Given a significant similarity between models of blood pressure disturbances and human disturbances, bepecin is justified in the therapy of blood pressure disturbances, hypertension and hypotension, and related disorders.

Example 27. Alcohol—Acute and Chronic Intoxication, Anaesthetics

Research of bepecin effectiveness in alcohol intoxications was performed by the use of methods described in Curr. Pharm. Des., 2010; 16 (10), 1224-1234; J. Physiol. Pharmacol., 2009, 60 (Suppl. 7), 177-181; Eur. J. Pharmacol., 1999,364 (1), 23-31; Life Sci., 1994, 54, (5), PL68; Dig. Dis. Sci., 1997.42 (5), 1029-1037.

Bepecin in doses ranging from 10 ng to 10 μg/kg body weight, parenterally or orally, prevented and inhibited the effect of alcohol acute intoxication, withdrawal, and acute and chronic gastric and liver lesions, as well as portal hypertension as a result of either acute alcohol consumption or prolonged chronic alcohol drinking. By analogy, bepecin antagonizes withdrawal symptoms in morphine-addicted mice. In addition, similarly like naloxon (10 mg/kg s.c.) bepencin antagonizes anesthetic action of morphine (16 mg/kg s.c.).

If alcohol is taken as a prototype, bepecin accordingly acts against the effects of propofol, thiopental and ketamine. It reduced the effect of both anaesthesia and catalepsy (i.e. fentanyl, dehydrobenzperidol).

Since consumption of alcohol produces similar effects also in humans, bepecin may be used in acute and chronic alcohol intoxication and withdrawal symptoms (also e.g. in morphine and similar substances), and also with anesthetics, to modulate their anaesthetic effect.

Example 28. Activity of Bepecin on Tumors

A common model for research of experimental tumors involves the assessment of the number of metastases of carcinoma and melanoma B-16 in mice. These experimental tumors have a considerable similarity with tumors in humans.

Ehrlich's ascites tumor (EAT) grows in all strains of mice and is commonly recognizably used in these experiments.

Mice infected with EAT tumor cells survived for a maximum of 25 days. Prior incubation of mice with bepecin (2 μg/ml) considerably prolonged animal survival, mostly to the end of observation (45 days). Bepecin also prevents the occurrence of neutropenia, reduces reticulocytes and improves hemoglobin values after the use of the cyclophosphamide cytostatic.

In Vitro Experiments

Figure 2:
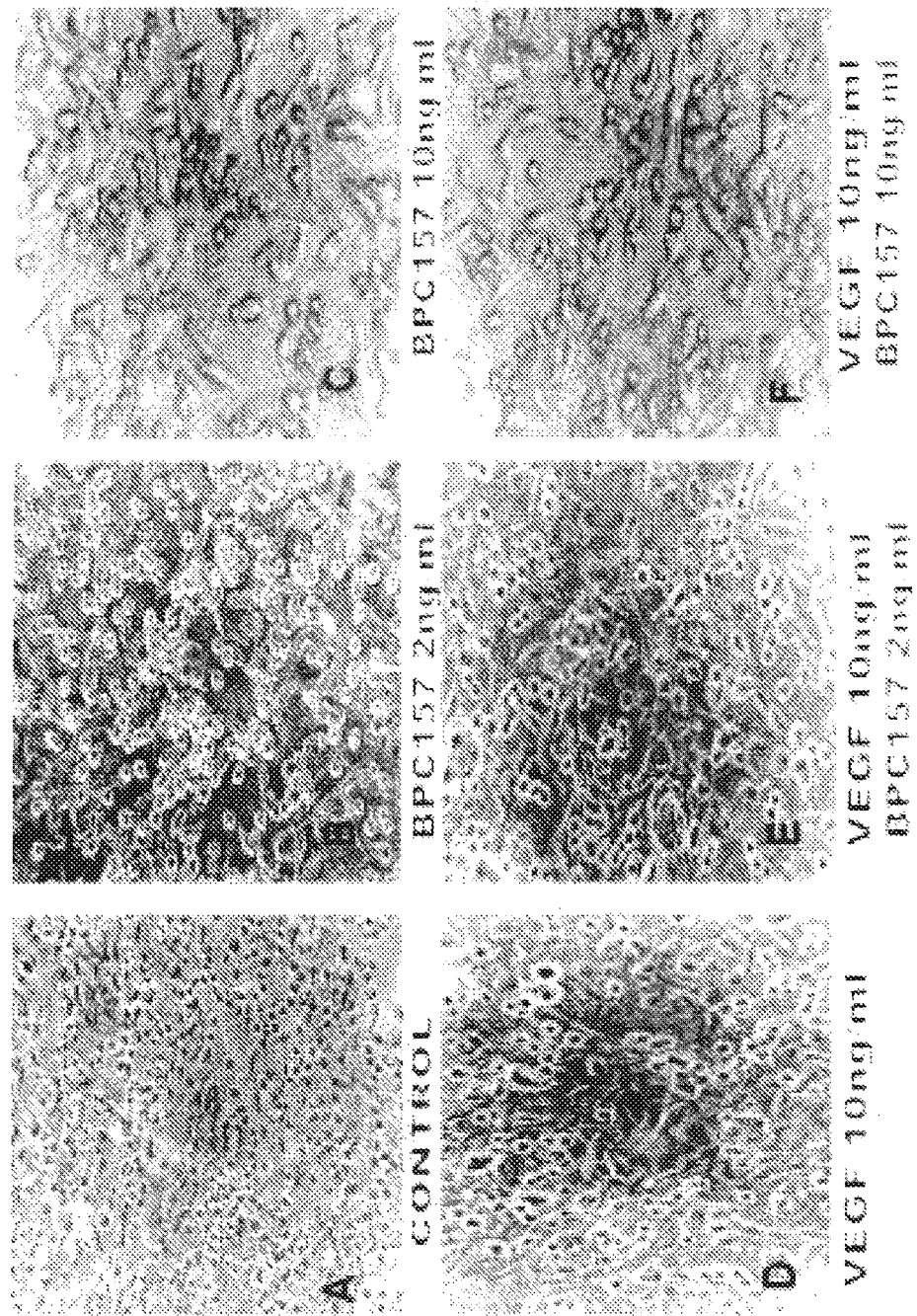
FIG. 2 Illustration of activity of bepecin to melanoma B-16 cells

The activity on melanoma cells was investigated in human melanoma cell culture in RPMI 1840 medium supplemented with a phosphate buffer and antibiotics. The cell culture was grown in an incubator at 37° C. and humid atmosphere with 5% of $CO_2$. To the well-grown cell culture bepecin was added in concentrations of 2 pg/ml, 2 ng/ml and 10 ng/ml, separately also in a combination with a vascular endothelial growth factor (VEGF—10 ng/ml) for a period of 48 hours. Cell morphology was observed by a light microscope and by flow cytometry. After an addition of bepecin to the cell culture the density of melanocyte cells was considerably decreased. In addition, cell phenotype was changed from round melanocyte cells to spindle-like epithelial cells with finely formed cellular interlacing. The most expressed results were evident at bepecin concentration of 10 ng/ml Similar changes were also observed in the case of cells first stimulated with VEGF and subsequently with bepecin. FIG. 2.

A flow cytometry analysis demonstrated that at a concentration of 2 pg/ml of bepecin, the number of cells in S-phase was reduced to 20% compared to control, and at concentrations of 2 ng/ml and 10 ng/ml of bepecin to 55%.

Western blot analysis revealed that bepecin acted antimitogenically by inhibiting mitogen-activated protein kinase (MAPK) responding to VEGF factor.

Bepecin has evidently expressed an anti-tumor potential. By considering the similarity between the animal models and human conditions and the beneficial results obtained in both in vivo and in vitro experiments, bepecin will be effective in anti-tumor therapy. It is also useful for reducing side effects of cytostatics.

Example 29. Gastrointestinal Tract Lesions

Methods and materials described in numerous publications (Curr. Pharm. Des., 2010, 16 (10), 1224-34; J. Physiol Pharmacol. 2009, 60 (Suppl. 7), 107-114; Dig. Dis. Sci.

2008, 108 (11), (7-17); Dig. Dis. Sci. 2009, 54 (1) 46-56) were used for determination of therapeutic activity of bepecin in doses ranging from 10 ng to 10 µg/kg (i.p., i.g.) in comparison with reference standards in several experimental ulcer models (e.g. 24 hour-restraint stress, subcutaneous or intrarectal cysteamine, instillation of 96% ethanol into stomach, NSAID-lesions, DNFB (dinitrofluorobenzene) lesions, reflux esophagitis in pre-, co- and post-treatment. In all of the models, bepecin was successfully used parenterally or orally.

Bepecin effectively inhibited the appearance of wounds and accelerated therapy of the existed ones in all models.

Given a considerable similarity with human disorders, bepecin can be successfully applied in the therapy of all gastrointestinal tract lesions.

Example 30. Potassium—Hypokalemia and Hyperkalemia

Potassium is of key importance for a normal function of heart smooth muscles, digestive tract, skeletal muscles and nerves. A normal potassium concentration is very important for the cardiac rhythm, thus both a too low concentration (hypokalemia) and a too high concentration (hyperkalemia) induce cardiac rhythm disorders and numerous other abnormalities in the organism.

By applying the methods described in J. Clin. Exp. Cardiolog. 2012, 3, 201; Regul. Pept., 2013, 181C, 50-66, furosemide (100 mg/kg, i.p.) was applied and then after 90-150 minutes the duration of PR, RR, QRS, QT intervals, P, R, S, T waves and their amplitudes were monitored electrocardiographically; further we analyzed the appearance of AV blockade, ventricular premature beats, ventricular tachycardia. Despite present hypokalemia, all bepecin (10 µg/kg and 10 ng/kg, i.p. and i.g.) regimens maintained sinus rhythm, had no ventricular premature beats, ventricular tachycardia, AV blockade, no prolongation of intervals and waves without reduction in amplitude. Bepecin was given 90 min after furosemide (with hypokalemia, 3rd grade AV blockade and/or ventricular tachycardia being present). Within 5-10 min, bepecin regimens normalized P, R, S, T waves, PR, RR, QRS, QT interval duration, R, S, T wave amplitude, total AV blockade and terminated ventricular tachycardia.

Using the methods described before in J. Pharmacol. Sci., 2007, 104 (1), 7-18; J. Pharmacol. Sci., 2006, 102 (3), 269-277 the full counteracting ability of bepecin against KCl-overdose (intraperitoneal (i), intragastric (ii), in vitro (iii)) was demonstrated. Thus, bepecin could be useful as an original therapy to normalize all disorders that appear along with the manifestation of hypokalemia and hyperkalemia.

Example 31. Calcium—Hypercalcemia

Calcium has an important role in the organism since it acts on the cells of the heart muscle, blood vessels and neurons. The most frequent cause of a too high level of calcium—hypercalcemia—is primary hyperparathyroidism, and the second cause is malignancy and granulomatosis. Hypercalcemia may result in various disorders such as hypertension, calcification of soft tissues and eye cornea, nephrolithiasis and peptic ulcer.

Pathophysiological calcemia may be caused by diseases that increase osteoclast activity and bone reabsorption, which the kidneys are not able to follow. It may occur also at vitamin D overdose and by use of calcium substitutes—antacids and thiazide diuretics. A very widespread cause is often the use of calcium channel blockers in patients with hypertension.

Bepecin was shown to be effective in hypercalcemia, counteracting the effect of $CaCl_2$ overdose. Likewise, bepecin can counteract the effects of calcium channel blocker overdose.

A calcium overdose and prolonged hypercalcemia namely induce acute pancreatitis and a shortening of $QT_c$ interval and prolongation of PQ interval in rats. The rats received a $CaCl_2$ solution (200 mg and 400 mg/kg, i.p.). Continuously, ECG was recorded and K, Na, Cl, amylase, creatine kinase and LDH (at 5, 10, 15, 25 and 60 min) and acute pancreatitis at 60 min were determined as described in Dig. Dis. Sci., 1996, 41 (7), 1518-1526; Regul. Pept., 2009, 156 (1-3), 83-89; J. Pharmacol. Sci., 2004, 95 (1), 19-26. Bepecin (10 µg/kg, i.p.) was administered also prophylactically 30 min before $CaCl_2$. The rats received a bolus of verapamil (40 mg/kg, i.p.). Bepecin (10 µg/kg and 10 ng/kg, i.p.) was administrated 30 min before verapamil (pre-treatment) or as a post-treatment 5 min after.

Bepecin counteracted the consequence of severe hypercalcemia, eliminated both shortening of $QT_c$ interval and prolongation of PQ interval and counteracted otherwise severe acute pancreatitis, and decreased the value of serum amylase.

After 5 min verapamil induced bradycardia (200-230/min) together with the 2' degree atrioventricular block lasting for 30 and 45 min. With bepecin sinus rhythm was retained or recovered (in therapeutical application atrioventricular block was also eliminated).

Experiments demonstrated that bepecin prevents or reverses all consequences of hypercalcemia. Thus, bepecin could be useful as an original therapy to normalize all disturbances that appear along with the manifestation of hypercalcemia.

Example 32. Influence on Myastenic Syndrome

Myastenic syndrome, manifested in increased muscle relaxation with a huge number of different drugs known to aggravate myasthenia gravis, was induced in accordance with Acta Neurol. Scand., Suppl., 1984, 100, 39-47 using intraperitoneal administration of an overdose of magnesium sulfate. Male and female rats, 200-300 g body weight that received magnesium sulfate (500 mg/kg body weight, i.p.), presented a prominent myasthenia, already after 5 min (progressive weakness, prostration, weakness in muscles) progressing toward complete immobility. Bepecin was applied 15 min before or simultaneously with magnesium sulfate (10 µg/kg and 10 ng/kg body weight, i.p.) and completely counteracted magnesium-sulfate disturbances, and all animals were normally active.

Treadmill running tests reveal that after application of bepecin in normal rats their performance is improved and they can run much longer than before.

Thus, in general, bepecin can be useful as an original therapy to normalize all disorders that appear as a myastenic syndrome, and in particular, to counteract all disorders that appear along with the therapy with magnesium. Likewise, bepecin may be an original therapy to improve the skeletal muscle function in general.

Example 33. Influence on Neuromusculatory and Neuropsychiatric Disorders

Dopamine system is commonly thought to be essential for motor functions (J. Neural. Transm. 2010 December; 117

(12):1359-69). Using previously described methods in Life Sci. 2001 Mar. 9; 68(16), 1905-12. J. Physiol. Paris. 2000 March-April; 94(2), 105-110 it was demonstrated that bepecin may strongly interact with dopamine system, in a particular way, providing that it counteracts the consequences of dopamine receptors blockade, catalepsy and somatosensory disorders induced by different neuroleptics such as haloperidol, flufenazin and clozapine, dopamine vesicles depletion, nigrostriatal dopamine destruction induced by neurotoxin 1-methyl-4-phenyl-1,2,3,6-tetrahydropyridine (MPTP). Bepecin strongly improved the MPTP-impaired somatosensory orientation and reduced the MPTP-induced hyperactivity, and most importantly, MPTP-motor abnormalities (tremor, akinesia, catalepsy—otherwise very prominent in saline control), leading to almost complete abolition of otherwise regularly lethal course of MPTP treatment in controls. As mentioned before, bepecin strongly improves muscle healing after muscle transection or contusion and nerve healing after nerve transection without or with anastomosis. Consequently, this may imply that bepecin may also be suitable to improve neuromuscular junction disability and signal transmission from nerve to muscle.

In fact, bepecin could be used to improve muscle functions disabilities in general. Considering the common significance of the mentioned dopamine and serotonin systems in animal models and human disorders, bepecin could be used in corresponding neuropsyhiachiatric disorders, particularly those related to dopamine and/or serotonin systems.

Example 34. Insulin—Diabetes

Using the procedures described previously in Skin. Pharmacol. Physiol. 2006, 19(5), 266-274, J. Physiol. Paris, 1999 December; 93(6), 501-4, bepecin given topically may significantly increase healing of skin wounds in diabetic animals. It was further demonstrated that bepecin inhibits development of alloxan-induced ulcer, hypertension induced by fructose intake, and insulin resistance. Similarly, bepecin (10 μg/kg) applied (i) intraperitoneally or (ii) intragastrically immediately after insulin, as an antiulcer peptide, may besides stomach ulcer consistently counteract all insulin (over-dose of 250 IU/kg i.p.) disorders and fatal outcome (i.e. seizures (eventually fatal), severely damaged neurons in cerebral cortex and hippocampus, hepatomegaly, fatty liver, breakdown of liver glycogen with profound hypoglycemia. Thus, the success of bepecin therapy may indicate a potential role of bepecin in insulin monitoring, and bepecin may influence one or more causative process(es) after an excessive insulin application, thereby its application to control various disturbances in diabetic patients, and particularly (ab)use of insulin therapy.

Example 35 Antiinflammatory Activity, Pain and Temperature

Based on the evidence largely reviewed (J. Physiol. Paris. 1993; 87, 313-27, Inflammopharmacol. 2006; 14, 214-21, Curr. Pharm. Des. 2010; 16, 1224-34) bepencin was proved to reduce the release of inflammatory mediators (i.e. myeloperoxidase, leukotriene $B_4$, thromboxane $B_2$) both in vitro and in vivo. Bepecin successfully antagonized several models of acute, non-specific inflammation (i.e. carrageenan, turpentine, cotton pellet) as well as DNFB-injuries. Moreover, bepecin acts against temperature decrease (i.e. water immersion test) and increase (yeast-induced). Consistently, bepecin antagonized both inflammatory pain (acetic acid), and non-inflammatory pain ($MgSO_4$). Further, bepecin increases pain threshold in carrageenan test in rats and exhibits an anti-hyperalgesic effect in Randall-Selitto test.

In case of a transected sciatic nerve, without and with anastomosis, bepecin strongly reduces neuropathic pain.

The effect of bepecin on chronic inflammation lesions, such as adjuvant arthritis (induced in animals with Freund's adjuvants) and non-steroidal anti-inflammatory agents (NSAIAs) induced gastrointestinal lesions was simultaneously studied in rats and was found as very persuasive.

In the treatment of well-developed adjuvant arthritis, the beneficiary effect of bepecin is evident as early as after 2 weeks of treatment and it could be clearly seen even after one year after application.

Accordingly, bepecin may be used as an original therapy to reduce negative sequelae of acute and chronic inflammation, to normalize body temperature, and particularly to reduce pain.

Example 36. Effect on Nerve Injury

Using the methods previously described in Regul. Pept., 2010 Feb. 25; 160(1-3), 33-41, a healing of a transected sciatic nerve in rats and an improvement achieved by the application of bepecin (10 μg/kg, 10 ng/kg) applied shortly after the injury (intraperitoneally/intragastrically/locally) at the site of anastomosis was shown. The improvement was shown clinically (autotomy), microscopically/morphometrically and functionally (EMG, one or two months post-injury, walking recovery at weekly intervals). Bepecin-treated rats exhibited faster axonal regeneration: histomorphometrically (increased density and size of fibers, epineural and perineural regeneration, increased diameter of myelinated fibers, thickness of myelin sheet, number of myelinated fibers per area), electrophysiologically (increased motor action) and functionally (improved factor SFI).

Thus, bepecin markedly improved healing of the sciatic nerve in rats. Considering the noted similarity between experimental models and human pathology, these findings may be practically useful in the therapy of various nerve injuries.

Example 37. Somatosensory Neurons, Motor Nerve Injuries, Brain Injuries and Interrupted Signal Transmission on Relation Nerves/Muscle Either dysfunction or hyperfunction of somatosensory neurons was evidenced in a variety of disorders such as congenital neurosensory neuropathy caused by diabetes, herpes zoster, postherpetic neuralgia, atopic dermatitis, disturbed healing of injured tissue, psoriasis, eczema, asthma, chronic arthritis etc.

The somatosensory neurons are a system of the first defence line against trauma. They control the homeostasis and also initiate appropriate measures in case of danger. Their protective ability was evidenced by experimental damages of the skin and gastrointestinal mucosa with capsaicin. This substance given in high doses decomposes sensory fibers, whereas a low dose (below 0.5 mg/kg) activates neurotransmitter release and has a protective effect on the mucosa. In the experiment described in Dig. Dis. Sci., 1996, 41(8), 1604-1614, a high dose of capsaicin was used which decomposed the sensory fibers. Bepecin used in doses from 10 ng to 10 μg/kg of animal body weight, administered orally or locally, strongly decreased the effect of capsaicin.

Bepecin also strongly decreased the consequences of animal brain injuries induced by a falling weight. The model is described in Regulat. Pept., 2010, 160 (1-3), 26-32. An experiment with a succinylcholine injection (0.2 mg/kg) into the right muscle—quadriceps—also induced a neuromuscular disorder in the muscle action due to a failed signal transmission from nerve to muscle. Bepecin administered before or after succinylcholine injection entirely eliminated the local effect of succinylcholine.

By considering the neuroprotective effect of bepecin, the noted similarity between the experimental models and human pathology, these findings may be practically applicable in an enhanced clinical performance in the therapy of various nerve injuries.

Example 38. Effect on Encephalopathies and Multiple Sclerosis

By using the methods described previously in (Eur. J. Pharmacol. 2011, 667, 322-9; Life Sci. 2011, 88, 535-42; J. Physiol. Pharmacol. 2010, 61, 241-50; J. Physiol. Pharmacol., 2009, 60 Suppl. 7, 107-14; Regul. Pept., 2010, 160, 26-32 it was demonstrated that bepecin acts against all factors consequently leading to encephalopathy with an overdose of NSAIDs. It further acts against brain lesions that appear after a huge dose of insulin administration. Bepecin fully acts against the life-threatening insulin toxicity and fatal seizures, severely damaged neurons in cerebral cortex and hippocampus. Bepecin may further reduce brain damage resulting from trauma. At present, natalizumab, a humanized monoclonal antibody against the cell adhesion of α4-integrin molecules, is advantageously used in the treatment of multiple sclerosis and Crohn's disease. Considering the previous application of bepecin and its effectiveness in various models of ulcerative colitis, the already-mentioned bepecin effectiveness in the therapy of damaged muscles, nerves and brain injuries, a beneficial effect of bepecin may be anticipated on a suitable model for multiple sclerosis.

Among various experimental models of allergic encephalitis, cuprizone was claimed to be the most reliable one. A recently described protocol was used (J. Physiol. Pharmacol. 2013, Brain, 2006, 129, 1940-1952). Wistar rats were administered 2.5% of cuprizone in their diet regimen combined with an addition of bepecin to their drinking water 10 μg/kg or 10 ng/kg, 0.16 μg/ml/12 ml/day/rat or 0.16 ng/ml/12 ml/day/rat until euthanasia after four days; they were additionally given cuprizone 1 g/kg intragastrically once daily, and bepecin was given 10 μg/kg or 10 ng/kg intragastrically. Thus, the rats were repeatedly given higher doses of cuprizone in their food, which accelerated formation of damages. As a result nerve damage was observed in various parts of the brain, most prominent damage occurred in corpus callosum, laterodorsal thalamus and nucleus reunions. The rats treated with cuprizone and bepecin experienced consistently less nerve damage was in all parts. Bepencin showed the most beneficial effect in those parts which were the most affected. Consequently, based on the results of experiments bepencin proves to be suitable for the treatment of both inflammatory bowel disease and multiple sclerosis. Bepecin might further be the primary therapy in various encephalopathies.

Example 39. Antiviral Activity

Arboviruses, Hepatitis, Herpes and LCM Viruses

Antiviral activity was investigated in newborn 24-hour old BALB-C strain mice, male and female. Arboviruses (TBE=Tick-Borne Encephalitis virus, Bhanja, Dengue types 1, 2, 3 and 4, Sindbis, West Nile and Čalovo viruses), hepatitis A virus, Lymphatic Choriomeningitis (LCM) virus and herpes virus types 1 and 2 were used i.c. (or p.o. in hepatitis A) as virus suspension in a dilution of $10^{-2}$ (0.02 ml/mouse). Doses were adjusted to be comparable regarding $LD_{100}$ at 0.02 ml i.c. (or p.o. in hepatitis A)/mouse and inoculate in dilution $10^{-2}$. Bepecin (20 μg/kg body weight) or 0.9% NaCl solution (0.02 ml/mouse) were used i.c. or i.p. as follows:
(i) treatment 2 hours before viral infection (–2 h),
(ii) simultaneously with the viral infection (0)
(iii) 4 days later in the presence of infection symptoms.

The results are shown in Table 7.

When bepecin was applied before viral infection (i) no signs of disease or death at the time of observation were noted. If bepecin was administered concomitantly with infection (ii), disease symptoms appeared at a considerably later stage, after 20 days (in the control group without bepecin all animals died within 5 days). If bepecin was given in the presence of the first symptoms, the outbreak of the disease was significantly delayed (iii). Numbers in Table 7 represent time in days when all infected animals died (including control group). In a second control group consisting of healthy untreated animals there were no death cases. Sign "+" indicates oral dosage, sign "a" indicates ARBO virus and sign "n. d." means there were no death cases. All animals were observed 40 days after the infection.

Tick-Borne Encephalitis Virus

Figure 3:
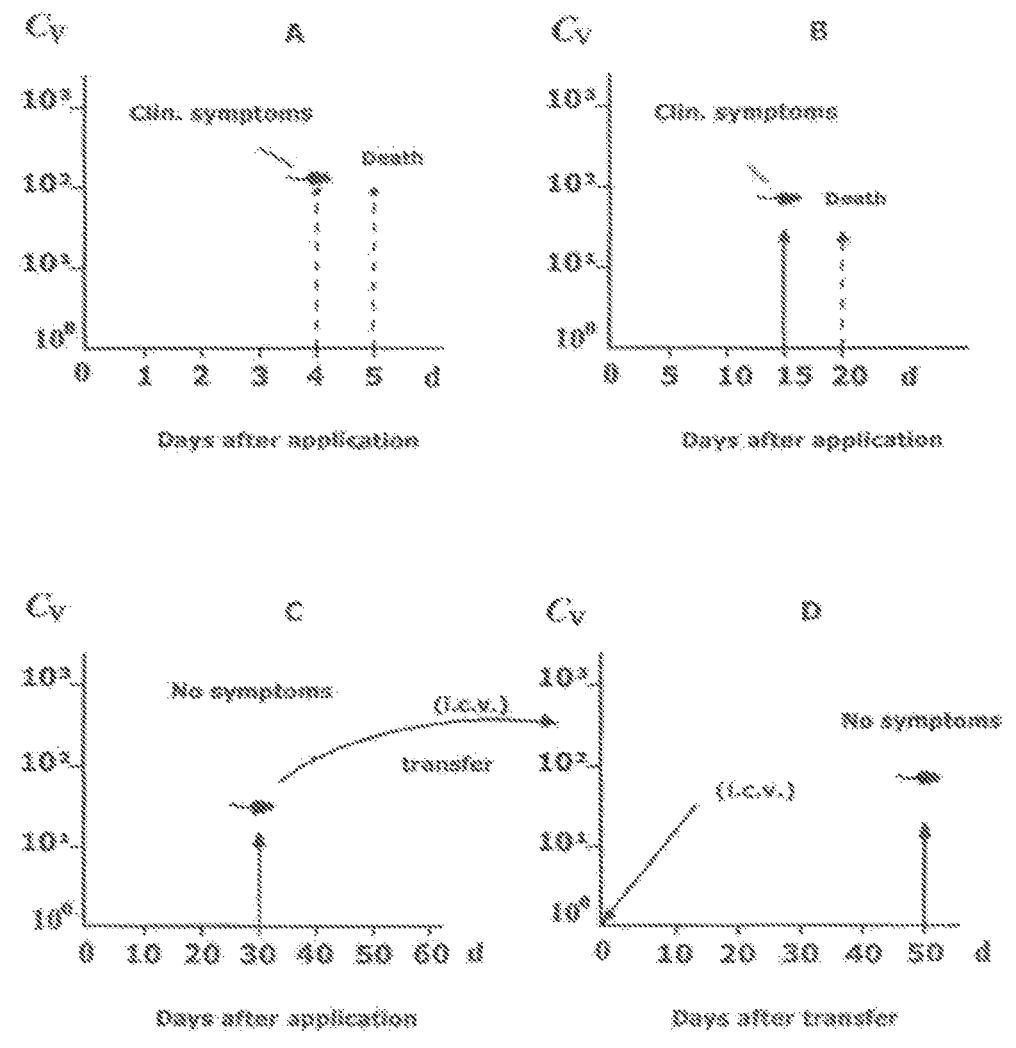

The activity of bepecin against tick-borne encephalitis virus in test mice is evidently demonstrated in FIG. 3. Bepecin was used in a dose of 0.02 mg/kg of body weight. Bepecin considerably prolongs the survival of test animals or even prevents infection by use of a suitable dosage.

To verify the results for virulence of the used viral suspension, part of brain tissue of an animal infected earlier with TBE virus and bepecin was taken and a brain homogenisate as a suspension was prepared. Using this suspension new animals were inoculated and infected with the new viral suspension (TBE). The treated animals did not show any symptoms of disease even after 50 days, whereas the animals that were only given saline instead the brain homogenisate died in 5 days.

TABLE 7

Time (days) to death after a viral infection of mouses Treatment of animals

| | Saline 0.9% | | | | Bepecin | | | |
|---|---|---|---|---|---|---|---|---|
| | Application ur 2 hours before viral infection (–2 h) | | Application concomitant with viral infection (0) | | Application 2 hours before viral infection (–2 h) | | Application concomitant with viral infection (0) | |
| Viral infection | ip | ic | ip | ic | ip | ic | ip | ic |
| TBE[a] | 5 | 5 | 5 | 5 | n.d. | n.d. | 20 | 20 |
| Bhania[a] | 5 | 5 | 5 | 5 | n.d. | n.d. | 20 | 20 |
| Dengue 1[a] | 5 | 5 | 5 | 5 | n.d. | n.d. | 20 | 20 |
| Dengue 2[a] | 5 | 5 | 5 | 5 | n.d. | n.d. | 20 | 20 |
| Dengue 3[a] | 5 | 5 | 5 | 5 | n.d. | n.d. | 20 | 20 |
| Dengue 4[a] | 5 | 5 | 5 | 5 | n.d. | n.d. | 20 | 20 |
| Sindbis[a] | 5 | 5 | 5 | 5 | n.d. | n.d. | 20 | 20 |
| West Nile[a] | 5 | 5 | 5 | 5 | n.d. | n.d. | 20 | 20 |
| Čalovo[a] | 5 | 5 | 5 | 5 | n.d. | n.d. | 15 | 15 |
| Hepatitis A+ | 5 | 5 | 5 | 5 | n.d. | n.d. | 20 | 20 |
| LCM[a] | 5 | 5 | 5 | 5 | n.d. | n.d. | 20 | 20 |
| Herpes HSV-1[a] | 5 | 5 | 5 | 5 | n.d. | n.d. | 20 | 20 |
| No infection | n.d. | n.d. | n.d. | n.d. | n.d. | n.d. | n.d. | n.d. |

Herpes Virus

A study with the use of VERO cells ($TICD_{50}$, HSV-1, $10^{10}$, $ID_{50/200 \mu l}$ and HSV-2: $10^{11}$, $ID_{50/100 \mu l}$, incubation for 24, 48 and 72 hours) has demonstrated that in in vitro cellular system inoculated with herpes viruses HSV-1 and HSV-2 bepecin inhibits reproduction of HSV virus and protects cells against cytopathogenic action HSV viruses.

Activity of bepecin "in vivo" was determined with experiments on newborn mice strain BALB/C using intracerebral inoculation with HSV-1 in concentration $10^{10}$ $ID_{50/100\ \mu l}$, and HSV-2 in concentration $10^{11}$ $ID_{50/100\ \mu l}$. Bepecin L-arginine salt was applied in doses of 10 µg/kg and 100 µg/kg. Groups of untreated animals served for comparison purposes; these animals were treated only with saline and acyclovir in doses of 10 mg/kg and 100 mg/kg. In one group all agents were applied 48 hours and in another 72 hours after a viral infection. The results show that bepecin remarkably reduces the number of sick animals in lethally infected mice and is more effective than the recognised medicine acyclovir. Survival time of the mice treated with acyclovir was 112/105/115 hours (medium/min./max.), whereas the survival time of the mice treated with bepecin (at smaller doses!) was significantly longer: 131/128/135 hours.

The efficiency of bepencin in doses of 10 µg/kg and 100 µg/kg proved to be better than that of acyclovir in considerably higher doses of 10 mg/kg and 100 mg/kg—under identical test conditions.

Similar results were obtained in case of infection with cytomegalovirus CMV.

Influenza A Virus

A study of the activity of bepecin on influenza A viruses, H1N1 and H3N2 types was performed on a MDCK model (Madin Darby Canine Kidney). As a culture medium MEM (Minimal Essential Medium) supplemented with 5% fetal bovine serum and antibiotics (Naruse N. et al., J. Antibiot., 1991, 44, 733-740) was used. Bepecin demonstrated a strong inhibitory effect on influenza A virus even at a very low concentration of 32 µg/ml and it was considerably more effective than hitherto known used compounds.

Feline Leukemia Virus

Feline leukemia virus (FeLV) is a retrovirus and as such transmitted as an RNA virus, but the RNA is reverse-transcribed into DNA. It is transmitted among cats with saliva or nasal secretions. The animal's immune system fails and the infection is lethal for the animal. The disease of this type is a type of blood lymphocyte cancer (leukemia).

The activity of bepecin was investigated (by a consent of owners) with tests performed on 32 cats (both genders) aged from 6 months to 5 years, which were not pre-vaccinated against this disease. All of them were in a strongly expressed disease stadium, Combo FeLV/FIV test was positive. All animals had high body temperature up to 41.5° C. as well as signs of severe disease: icterus, diarrhea, tachycardia, abdominal pain, dehydration and depression.

After being diagnosed, all cats received a bepecin solution in the form of a subcutaneous injection in a dose of 1 µg/kg of body weight (in 1 ml) once a day for the first 8 days, then the same doses perorally up to a total of one month.

Improvement was observed immediately, body temperature decreased just in 30 min for min. 1° C. and the general condition recovered within one week. However, the condition in some animals was again temporarily worse after 4-5 days for 24 hours, but improved again on day 6 and then complete recovery was observed in about 10 days.

Conclusion: cats which were not preventively vaccinated and became ill for feline leukemia can completely recover within 10 days if administered a daily bepecin dose of 1 µg/kg of body weight. Hitherto, there was no efficient medicine against this disease except vaccination and a very expensive interferon-omega.

On the basis of similar genetics of subtypes of viruses bepecin can be anticipated to be effective in cases of some other viral infections, e.g. herpes varicele zoster (VZV or HHV-3), Epstein-Barr (EBV) virus, human herpes viruses HHV-6, HHV-7, HHV-8 (Kaposi) and Chikungunya (CHIKV).

Considering the fact that some of these viruses induce similar disease phenomena also in humans, we believe that bepecin may be used in the therapy of these diseases also in humans, especially where the aspects for the patients are very unfavourable (e.g. AIDS and AIDS-related syndromes).

Example 40. Sphincter Action

An experimental testing method is specifically described in J. Pharmacol. Sci., 2007, 104 (1), 7-18 and J. Pharmacol. Sci., 2006, 102 (3), 269-277 and Regul. Pept., 2013. 181C, 50-66. Bepecin (10 ng/kg to 10 µg/kg of body weight, parenterally or orally) was found to retain sphincter function in rats (esophageal sphincter, pyloric sphincter and urethral sphincter), and pressure within sphincter, which would be otherwise disturbed. Moreover, bepecin may also rapidly recover sphincter function and its pressure even after long-lasting disorders (i.e. esophagitis, acute pancreatitis), or after different stress urinary incontinence procedures. In addition, bepecin also alleviated and eliminated esophagitis and other disorders resulting from sphincter failure (acute pancreatitis; different stress urinary incontinence).

Thus, considering the similarity of the used models and human pathology, bepecin may be an original therapy for all disorders related to failed sphincter function.

Example 41. Weight Gain in Animals—Veterinary Medicine

By using the methods described in Dig. Dis. Sci., 2009, 54 (1), 45-56, rats with an advanced short bowel syndrome and progressive weight loss following extensive small bowel resection were studied for 4 weeks. Postoperatively, the exhaustion of animals was increased with concomitant body weight decrease, twofold increase in crypt depth, fourfold increase in muscle thickness within the first week, jejunal and ileal dilatation and disturbed jejunum/ileum ratio Immediately after bepecin application a constant weight gain was observed and the following increased: villus height, crypt depth and muscle thickness (circular muscular layer). Rats treated with bepecin in doses of 10 ng/kg to 10 µg/kg of body weight, i.m. or p.o., did not have a difference in jejunal and ileal diameters. They had a constant jejunum/ileum ratio and an increased anastomosis breaking point. Accordingly, piglets treated with said doses of bepecin from day 1 to day 21 had a substantially better weight gain and no diarrhea.

Thus, considering the similarity of the used models and animal pathology, bepecin may be an original therapy in all disorders related to short bowel function. Further, bepecin could be accordingly used to improve weight gain, also in farm animals.

Example 42. Influence of Bepecin to Sperm Preservation

It is generally known that sperm freezing process in the preservation of sperm causes approximately a 50% decrease in the motility of sperm due to a temperature change and osmotic effect. Morphological changes occur due to organization, permeability, and lipid composition of spermium membranes.

We have found a beneficial action of bepecin on the motility of bull's sperm, which was frozen according to a slightly modified standard method (the medium was added bepecin before freezing).

The first part of the experiment was intended to determine the effect of in vitro most effective bepecin dose, which was 20 ng/ml, on the quality of sperm after thawing if the sperm was treated in such manner before freezing. The second part studied the effect on the shape of the sperm. The results were evaluated by a phase-contrast microscope and by CASA computer processing.

The treatment with bepecin before freezing of the medium improved the post-thaw motility at 37° C. compared with the control sperm sample (p<0.05; subjective method: p=0.0046; CASA: p=0.014).

Co-treatment of the sperm with bepecin immediately after thawing improved its motility compared with the control sample (p<0.05; subjective method: p=0.0018; CASA: p=0.014).

Considering the results it can be concluded that freezing of bull's sperm with the addition of bepecin had a very good effect on the in vitro quality of the sperm post-thawing. To confirm these results a further in vivo investigation would be beneficial.

Conclusion: according to the currently available results bepecin has a favourable effect on the quality of sperm in cryopreservation.

Example 43. Effect after Blood Vessel Extirpation

Bepecin has a particular beneficial effect after large blood vessel removal. Unlike L-NAME and L-arginine, bepecin rapidly bridges defect between the stumps of the vessel, thus even in the case of the worst scenario, rapidly reorganizing blood supply. Part of femoral artery in rats (between a. epigastrica caudalis and a. femoralis circumflexa lateralis) was removed in order to investigate collateral vessel presentation within vascular defect following formation of critical size vascular defect. Collateral vessel presentation within vascular defect was assessed according to the method described for microangiographic assessment in Cardiovasc Res. 1997 September; 35(3): 547-52. Thermographic imaging was performed using an infrared camera.

Figure 5A:
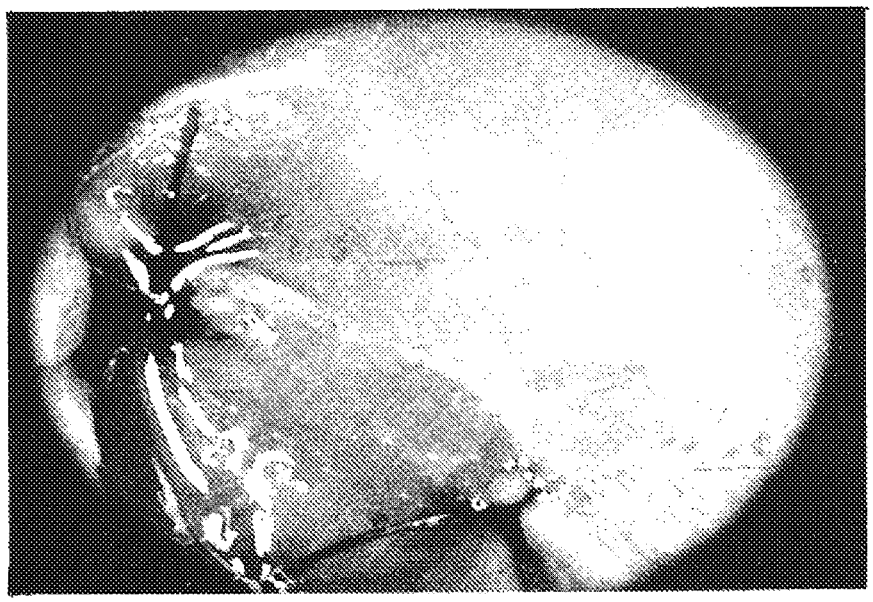
FIG. 5 Illustration of collateral blood vessels:
  A: a control group was subject only to a local saline bath for 1 min—no collateral vascular vessels are visible.

No collateral vessel presentation within vascular defect was observed in control group 5-10 min after the removal of the defined part of femoral artery in rats that received a local 1 min bath of saline (1 ml/rat, 5 ml/kg) immediately after the appearance of a vascular defect. FIG. 5A.

Tiny collateral vessels were present, yet without interconnections, within the vascular defect 5-10 min after the removal of the defined part of femoral artery in rats that received a local 1 min bath of L-arginine (1 ml/rat, 100 mg/kg) immediately after the appearance of a vascular defect.

The area of the vascular defect is completely empty and no collateral vessels are present within the vascular defect 5-10 min after the removal of the defined part of femoral artery in rats that received a local 1 min bath of L-NAME (1 ml/rat, 5 mg/kg) immediately after the appearance of a vascular defect.

Figure 5B:
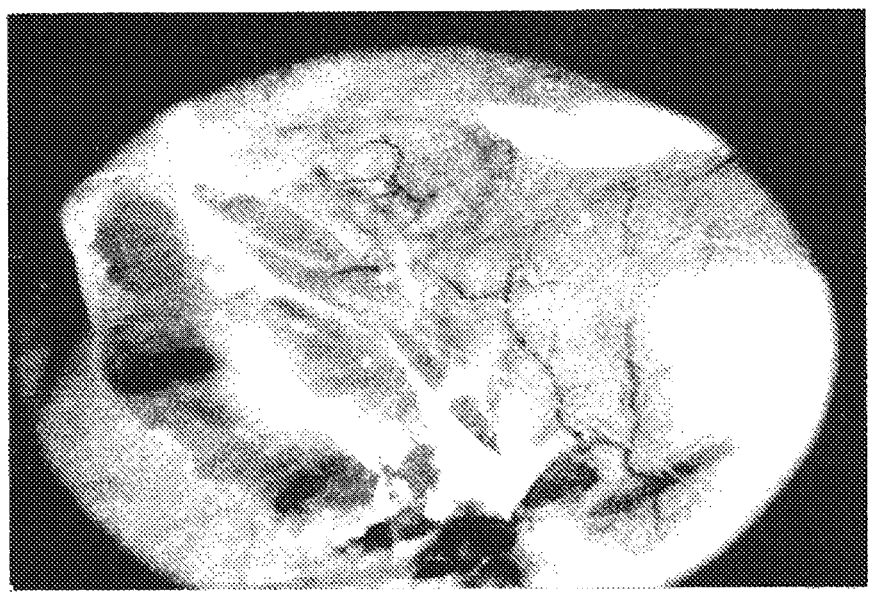

In the case of bepecin application, collateral vessels with full interconnections forming a bridging network and functional network can be observed (confirmed by thermographic recording) within the vascular defect 5-10 min after the removal of the defined part of femoral artery in rats that received a local 1 min bath of bepecin (1 ml/rat, 10 µg/kg) immediately after the appearance of the vascular defect. FIG. 5B.

This evidence shows that bepecin-mediated adaptation appears within existing collateral arteries rapidly after the removal of femoral artery and occlusion in order to restore vascular conductance and hence limb blood flow. In fact, a late adaption is arteriogenesis which is a process of collateral artery remodelling, while an early adaptation is vasodilation J. Vasc. Surg. 2010 January; 51(1): 165-73. Anyway, the clear distinction between L-arginine and bepecin proves that the early adaptation (currently investigated in day-periods (and not minute-periods) after vascular injury and not within the vascular defect itself) is not a simple vasodilatation, but a particular bepecin-mediated bridging process. We can talk of an important process that has a considerable effect on the initial increase in blood flow through collaterals in a way to become permanent. Consequently a highly advanced stage and the improved final outcome (formation of vascular tree from both stumps) are reached. Based on the experiment results, bepecin may be an original therapy for all conditions where a rapid reorganization of blood supply would be mandatory.

Example 44. Acute Toxicity

In all of the studies, bepecin demonstrated a very safe profile. Bepecin as di-L-arginine salt (1:2), as well in all other salt forms, given to both male and female Wistar Albino rats, in quite high dose regimen, i.e., 1 g/kg body weight, intraperitoneally, intravenously or intragastrically, demonstrates no toxicity and no adverse effects.

The invention claimed is:

1. A stable pentadecapeptide salt comprising formula (I), wherein formula (I) is:

SEQ ID NO: 1·2 BAA wherein BAA represents a basic amino acid.

2. The stable pentadecapeptide salt according to claim 1, wherein a basic amino acid is selected from the group consisting of arginine, lysine and ornithine.

3. The stable pentadecapeptide salt according to claim 2, wherein a basic amino acid represents arginine.

4. The stable pentadecapeptide salt according to claim 2, wherein a basic amino acid represents lysine.

5. The stable pentadecapeptide salt according to claim 2, wherein a basic amino acid represents ornithine.

6. A pharmaceutical formulation in a solid form for oral, rectal, vaginal and local use containing a therapeutically effective amount of pentadecapeptide salt according to formula I of claim 1.

7. The pharmaceutical formulation according to claim 6, wherein the pharmaceutical formulation further contains one or more antibiotics.

8. The pharmaceutical formulation according to claim 6, wherein the pharmaceutical formulation further contains one or more antioxidants.

9. The pharmaceutical formulation according to claim 6, wherein the pharmaceutical formulation further contains additives for increasing stability.

10. The pharmaceutical formulation according to claim 9, wherein the additive for increasing stability is sodium hydrogen carbonate.

11. The pharmaceutical formulation according to claim 10, wherein the sugar for increasing stability is D-mannitol.

12. The pharmaceutical formulation according to claim 6, wherein the pharmaceutical formulation further contains sugar for increasing stability.

13. A pharmaceutical formulation in a liquid form for oral, intravenous, intramuscular and local use containing a therapeutically effective amount of pentadecapeptide salt according to formula I of claim 1.

14. The pharmaceutical formulation according to claim 13, wherein the pharmaceutical formulation further contains one or more antibiotics.

15. The pharmaceutical formulation according to claim 13, wherein the pharmaceutical formulation further contains one or more antioxidants.

16. The pharmaceutical formulation according to claim 13, wherein the pharmaceutical formulation further contains additives for increasing stability.

17. The pharmaceutical formulation according to claim 16, wherein the additive for increasing stability is sodium hydrogen carbonate.

18. The pharmaceutical formulation according to claim 17, wherein the sugar for increasing stability is D-mannitol.

19. The pharmaceutical formulation according to claim 13, wherein the pharmaceutical formulation further contains sugar for increasing stability.

20. A process for the preparation of a stable pentadecapeptide salt comprising formula (I), wherein formula (I) is:

SEQ ID NO: 1·2 BAA wherein BAA represents a basic amino acid,
comprising reaction of pentadecapeptide according to SEQ ID NO: 1 with basic amino acid under stirring of the solution, adjusting pH value and isolation of the salt formed by high performance liquid chromatography and lyophilisation of the solution.

21. The process according to claim 20, comprising
reacting pentadecapeptide according to SEQ ID NO: 1 with arginine in a molar ratio of 2 mol arginine to 1 mol of pentadecapeptide in an aqueous solution at room temperature to form a formed solution;
adjusting the pH value of the formed solution by titration to form a pH adjusted solution;
isolating a salt formed of formula (I) by high performance liquid chromatography and lyophilisation.

22. The process according to claim 21, wherein the pH value of the solution obtained by a reaction of 2 mol of arginine with 1 mol of pentadecapeptide (SEQ ID NO: 1) is adjusted to between 6.7 and 7.8.

23. The process according to claim 22, wherein the pH value of the solution obtained is adjusted to 7.40±0.05.

24. The process according to claim 21, further comprising the step of adding the pentadecapeptide salt to food.

25. The process for the preparation of a stable pentadecapeptide salt according to claim 20 comprising
reacting pentadecapeptide according to SEQ ID NO: 1 with lysine in a molar ratio of 2 mol lysine to 1 mol of pentadecapeptide in an aqueous solution at room temperature to form a formed solution;
adjusting the pH value of the formed solution by titration to form a pH adjusted solution;
isolating a salt formed of formula (I) by high performance liquid chromatography and lyophilisation.

26. The process according to claim 25, wherein the pH value of the solution obtained by a reaction of 2 mol of lysine with 1 mol of pentadecapeptide (SEQ ID NO: 1) is adjusted to between 6.7 and 7.8.

27. The process according to claim 26, wherein the pH value of the solution obtained is adjusted to 7.40±0.05.

28. The process according to claim 25, further comprising the step of adding the pentadecapeptide salt to food.

29. The process for the preparation of a stable pentadecapeptide salt according to claim 20, comprising
reacting pentadecapeptide according to SEQ ID NO: 1 with ornithine in a molar ratio of 2 mol ornithine to 1 mol of pentadecapeptide in an aqueous solution at room temperature to form a formed solution;
adjusting the pH value of the formed solution by titration to form a pH adjusted solution;
isolating a salt formed of formula (I) by high performance liquid chromatography and lyophilisation.

30. The process according to claim 29, wherein the pH value of the solution obtained by a reaction of 2 mol of ornithine with 1 mol of pentadecapeptide (SEQ ID NO: 1) is adjusted to between 6.7 and 7.8.

31. The process according to claim 30, wherein the pH value of the solution obtained is adjusted to 7.40±0.05.

32. The process according to claim 29, further comprising the step of adding the pentadecapeptide salt to food.

33. A method for prevention, protection and treatment of at least one of a plurality of diseases, disease conditions or disorders, comprising administering to an individual in need of such treatment therapeutically effective amount of a stable pentadecapeptide salt comprising formula (I), wherein formula (I) is:

SEQ ID NO: 1·2 BAA wherein BAA represents a basic amino acid, and
wherein the at least one of the plurality of diseases, disease conditions or disorders is one from the group consisting of:
stress related diseases and disorders,
ulcers in any part of gastrointestinal tract, generally antiinflammatory activity, gastrointestinal inflammatory disease, Crohn's disease and acute pancreatitis,
diseases, disease conditions or disorders in need of organoprotective activity,
viral infections comprising hepatitis A, herpes strains, influenza A and arthropode borne (ARBO) viruses, the ARBO viruses comprising tick borne encephalitis, West Nile fever, dengue types 1-4, cytomegalovirus (CMV) and lymphocytic choriomeningitis (LCM) virus, and feline leukemia virus, melanoma and related tumors, accelerated healing of wounds, burns, bone fractures, regeneration of ruptured nerve linkages, Achiles' tendon and ruptured muscles, spinal cord injury, organic disorders associated with nitric oxide (NO) formation: hypertension, hypotension, anaphylaxis, circulatory and septic shock, aggregation of thrombocytes, neurological diseases and disorders: multiple sclerosis, myasthenia gravis, lupus erythematosus, neuropathy, dysfunction of somatosensory nerves, asthma, rhinitis, pemphigus and eczema, catecholaminergic dysfunction, schizophrenia, amphetamine, drug and alcohol withdrawal effects, disorders due to corticosteroids and nonsteroidal anti-inflammatory drugs (NSAIDs), squamous degeneration of macula in eyes, rapid reorganisation of blood supply is mandatory, gain weight increment in animals and wherein the individual is an animal, an increase in sperm stability in storage and wherein the individual is an animal, and hepatic and pancreatic lesions.

\* \* \* \* \*